US007429659B2

(12) United States Patent
Carruthers et al.

(10) Patent No.: US 7,429,659 B2
(45) Date of Patent: Sep. 30, 2008

(54) FURAN COMPOUNDS AS HISTAMINE H₃ MODULATORS

(75) Inventors: Nicholas I. Carruthers, Poway, CA (US); Chandravadan R. Shah, San Diego, CA (US); Devin M. Swanson, La Jolla, CA (US)

(73) Assignee: Janssen Pharmaceutica N.V. (BE)

( * ) Notice: Subject to any disclaimer, the term of this patent is extended or adjusted under 35 U.S.C. 154(b) by 412 days.

(21) Appl. No.: 11/095,225

(22) Filed: Mar. 31, 2005

(65) Prior Publication Data

US 2005/0222129 A1    Oct. 6, 2005

Related U.S. Application Data

(60) Provisional application No. 60/557,936, filed on Mar. 31, 2004.

(51) Int. Cl.
 *C07D 243/08* (2006.01)
 *C07D 401/00* (2006.01)
 *C07D 403/00* (2006.01)

(52) U.S. Cl. .................... 540/575; 544/360; 544/366

(58) Field of Classification Search .................. None
See application file for complete search history.

(56) References Cited

U.S. PATENT DOCUMENTS

| 5,217,986 | A | 6/1993 | Pomponi et al. |
| 5,352,707 | A | 10/1994 | Pompni et al. |
| 5,869,479 | A | 2/1999 | Kreutner et al. |
| 7,067,507 | B2 * | 6/2006 | Pulley et al. ................. 514/183 |

FOREIGN PATENT DOCUMENTS

| JP | 10 017564 A | 1/1998 |
| WO | WO 99/12933 A2 | 3/1999 |
| WO | WO 99/12933 A3 | 3/1999 |
| WO | WO 00/53589 A1 | 9/2000 |
| WO | WO 2004/037801 A1 | 5/2004 |
| WO | WO 2004/054973 A2 | 7/2004 |
| WO | WO2005/018557 | * 3/2005 |

OTHER PUBLICATIONS

Vippagunta et al. Advanced Drug Delivery Reviews, 2001, 48, 3-26.*
Giuseppe et al. Expert Opinion on Therapeutic Patents, 1997, 7 (4), 307-323.*
Kitbunnadaj et al. Journal of Medicinal Chemistry, 2003, 46, 54455457.*
Camfield, C. and Camfield, P. Pediatrics, 2007, 120(1), e52-e55.*
Lee and Corren. Expert Opinion on Pharmacotherapy, 2007, 8(5), 701-709.*
"Attention Deficit Disorder", http://www.massgeneral.org/children/adolescenthealth/articles/aa_add.aspx, accessed Sep. 4, 2007.*
Lintunen et al. FASEB Journal, 2001.*
Brooks et al. Expert Opinion on Investigational Drugs, 2002, 11(12), 1821-27.*
Crow, Scott.. Expert Opinion on Investigational Drugs, 1997, 6(4), 427-36.*
Langran et al. Emergency Medicine Journal, 2004, 21, 728-741.*
Database Biosis "Online" Biosciences Information Service, Philadelphia, PA, US; 1988, Arrang J-M et al: "Phencyclidine Blocks Histamine H-3-Receptors in Rat Brian" (XP002351852). Database accession No. PREV198987074823 abstract & European Journal of Pharmacology, vol. 157, No. 1, 1988, pp. 31-36, ISSN: 0014-2999.
Stark H: "Recent advances in histamine H3/H4 receptor ligands", Expert Opinion on Therapeutic Patents (Jun. 1, 2003) United Kingdom, vol. 13, No. 6, Jun. 1, 2003, pp. 851-865 (XP002298271), ISSN: 1354-3776, p. 858.
International search report dated Nov. 24, 2005, for corresponding international application PCT/US2005/010632.
Arrang, J.-M. et al. Auto-inhibition of Brain Histamine Release Mediated by a Novel Class (H₃) of Histamine Receptor, *Nature* 1983, 302, 832-837.
Ash, A.S.F.; Schild, H.O. Receptors Mediating Some Actions of Histamine. *Br. J. Pharmac. Chemother.* 1966, 27, 427-439.
Barnes, J.C. et al. The Selective Histamine H3 Receptor Antagonist Thioperamide Improves Cognition and Enhances Hippocampal Acetylcholine Release in Vivo. *Soc. Neurosci, Abstr.* 1993, 19, 1813.
Black, J.W. et al. Definition and Antagonism of Histamine H₂-Receptors. *Nature* 1972, 236, 385-390.
Cardwell, K.S., et al. A New Method for the Formation of 2,4-Disubstituted Oxazoles: Internal Transfer of Oxidation State Through a Molecular Framework, *Tetrahedron Lett.* 2000, 41(21), 4239-4242.
Ganellin, C.R. et al. Synthesis of Potent Non-Imidazole Histamine H₃-Receptor Antagonists: *Arch. Pharm. Pharm. Med. Chem.* (Weinheim, Ger.) 1998, 331, 395-404.
Ichinose, M.; Barnes, P.J. Histamine H₃-Receptors Modulate Nonadrenergic Noncholinergic Neural Bronchoconstriction in Guinea-Pig In Vivo. *Eur. J. Pharmacol.* 1989, 174(1), 49-55.
Imamura, M. et al. Unmasking of Activated Histamine H₃-Receptors in Myocardial Ischemia: Their Role as Regulators of Exocytotic Norepinephrine Release. *J. Pharmacol. Exp. Ther.* 1994, 271(3), 1259-1266.
Krause, M. et al. Medicinal Chemistry of Histamine H₃ Receptor Agonists. In *The Histamine H₃ Receptor—A Target for New Drugs.* Leurs, R.; Timmerman, H., Eds.; Elsevier: 1998; pp. 175-196.
Letavic, M.A. et al. Recent Medicinal Chemistry of the Histamine H₃ Receptor. Prog. in Med. Chem., in press.
Leurs, R. et al. The Medicinal Chemistry and Therapeutic Potentials of Ligands of the Histamine H₃ Receptor. *Prog. Drug Res.* 1995, 45, 107-165.
Lin, J.-S. et al. Involvement of Histaminergic Neurons in Arousal Mechanisms Demonstrated with H₃-Receptor Ligands in the Cat. *Brain Res.* 1990, 523, 325-330.
Linney, I.D. et al. Design, Synthesis, and Structure-Activity Relationships of Novel Non-Imidazole Histamine H₃ Receptor Antagonists, *J. Med. Chem.* 2000, 43(12), 2362-2370.

(Continued)

*Primary Examiner*—James O. Wilson
*Assistant Examiner*—Noble Jarrell

(57) ABSTRACT

Certain furan compounds are histamine H₃ modulators useful in the treatment of histamine H₃ receptor mediated diseases.

23 Claims, No Drawings

OTHER PUBLICATIONS

Lovenberg, T.W. et al. Cloning and Functional Expression of the Human Histamine $H_3$ Receptor. *Mol. Pharmacol.* 1999, 55(6), 1101-1107.

Machidori, H. et al. Zucker Obese Rats: Defect in Brain Histamine Control of Feeding. *Brain Res.* 1992, 590, 180-186.

MacDonald, S.J.F. et al. Discovery of Further Pyrrolidine trans-Lactams as Inhibitors of Human Neutrophil Elastase (HNE) with Potential as Development Candidates and the Crystal Structure of HNE Complexed with an Inhibitor (GW475151). *J.Med.Chem.* 2002, 45(18), 3878-3890.

Mcleod, R.L. et al. Antimigraine and Sedative Activity of SCH 50971: A Novel Orally-Active Histamine $H_3$ Receptor Agonist. *Soc. Neurosci. Abstr.* 1996, 22, 2010.

Monti, J.M. et al. Effects of Selective Activation or Blockade of the Histamine $H_3$ Receptor on Sleep and Wakefulness. *Eur. J. Pharmacol.* 1991, 205(3), 283-287.

Morisset, S. et al. High Constitutive Activity of Native $H_3$ Receptors Regulates Histamine Neurons in Brain. *Nature* 2000, 408, 860-864.

Panula, P. et al. Significant Changes in the Human Brain Histaminergic System in Alzheimer's Disease. *Soc. Neurosci. Abstr.* 1995, 21, 1977.

Phillips, J.G. and S.M. Ali, Medicinal Chemistry of Histamine $H_3$ Receptor Antagonists. In *The Histamine $H_3$ Receptor—A Target for New Drugs*. Leurs, R.; Timmerman, H., Eds.; Elsevier: 1998; pp. 197-222.

Schlicker, E.; Marr, I. The Moderate Affinity of Clozapine at $H_3$ Receptors Is Not Shared by Its Two Major Metabolites and by Structurally Related and Unrelated Atypical Neuroleptics. *Naunyn-Schmiedeberg's Arch. Pharmacol.* 1996, 353, 290-294.

Stark, H. et al. Developments of Histamine $H_3$-Receptor Antagonists. *Drugs Future* 1996, 21(5), 507-520.

Tozer, M.J.; Kalindjian, S.B. Histamine $H_3$ Receptor Antagonists. *Exp. Opin. Ther. Patents* 2000, 10(7), 1045-1055.

Walczynski, K. et al. Non-Imidazole Histamine $H_3$ Ligands. Part I. Synthesis of 2-(1)Piperazinyl)- and 2-(Hexahydro-1H-1,4-diazepin-1-yl)benzothiazole Derivatives as H3-Antagonists with H1 Blocking Activities. *Farmaco* 1999, 54, 684-694.

Walczynski, K. et al. Non-Imidazole Histamine H3 Ligands, Part 2: New 2-Substituted Benzothiazoles as Histamine H3 Antagonists. *Arch. Pharm. Pharm. Med. Chem.* (Weinheim, Ger.) 1999, 332, 389-398.

Yokoyama, H. et al. Effect of Thioperamide, a Histamine $H_3$ Receptor Antagonist, on Electrically Induced Convulsions in Mice. *Eur. J. Pharmacol.* 1993, 234, 129-133.

* cited by examiner

FURAN COMPOUNDS AS HISTAMINE H$_3$ MODULATORS

This application claims priority to provisional application, which is U.S. Ser. No. 60/557,936 filed Mar. 31, 2004. The complete disclosures of the aforementioned related U.S. patent applications are hereby incorporated herein by reference for all purposes.

FIELD OF THE INVENTION

The present invention relates to a series of thiophenes, furans, pyrroles, thiazoles, and oxazoles, their synthesis and their use, for example, for the treatment of disorders and conditions mediated by the histamine H$_3$ receptor.

BACKGROUND OF THE INVENTION

Histamine {2-(imidazol-4-yl)ethylamine} is a transmitter substance. Histamine exerts a physiological effect via multiple distinct G-protein coupled receptors. It plays a role in immediate hypersensitivity reactions and is released from mast cells following antigen IgE antibody interaction. The actions of released histamine on the vasculature and smooth muscle system account for the symptoms of the allergic response. These actions occur at the H$_1$ receptor (Ash, A. S. F. and Schild, H. O., Br. J. Pharmac. Chemother. 1966, 27:427-439) and are blocked by the classical antihistamines (e.g. diphenhydramine). Histamine is also an important regulator of gastric acid secretion through its action on parietal cells. These effects of histamine are mediated via the H$_2$ receptor (Black, J. W. et al., Nature 1972, 236:385-390) and are blocked by H$_2$ receptor antagonists (e.g. cimetidine). The third histamine receptor —H$_3$— was first described as a presynaptic autoreceptor in the central nervous system (CNS) (Arrang, J.-M. et al., Nature 1983, 302:832-837) controlling the synthesis and release of histamine. Recent evidence has emerged showing that H$_3$ receptors are also located presynaptically as heteroreceptors on serotonergic, noradrenergic, dopaminergic, cholinergic, and GABAergic (gamma-aminobutyric acid containing) neurons. These H$_3$ receptors have also recently been identified in peripheral tissues such as vascular smooth muscle. Consequently, there are many potential therapeutic applications for histamine H$_3$ agonists, antagonists, and inverse agonists. (See: "The Histamine H$_3$ Receptor-A Target for New Drugs", Leurs, R., and Timmerman, H., (Eds.), Elsevier, 1998; Morisset, S. et al., Nature 2000, 408:860-864.) A fourth histamine receptor —H$_4$— was recently described by Oda, T. et al. (J. Biol. Chem. 2000, 275(47):36781-36786).

The potential use of histamine H$_3$ agonists in sleep/wake and arousal/vigilance disorders is suggested based on animal studies (Lin, J.-S. et al., Brain Res. 1990, 523:325-330; Monti, J. M. et al., Eur. J. Pharmacol. 1991, 205:283-287). Their use in the treatment of migraine has also been suggested (McLeod, R. L. et al., Soc. Neurosci. Abstr. 1996, 22:2010) based on their ability to inhibit neurogenic inflammation. Other applications could include a protective role in myocardial ischemia and hypertension where blockade of norepinephrine release is beneficial (Imamura, M. et al., J. Pharmacol. Exp. Ther. 1994, 271(3):1259-1266). It has been suggested that histamine H$_3$ agonists may be beneficial in asthma due to their ability to reduce non-adrenergic non-cholinergic (NANC) neurotransmission in airways and to reduce microvascular leakage (Ichinose, M. and Barnes, P. J., Eur. J. Pharmacol. 1989, 174:49-55).

Several indications for histamine H$_3$ antagonists and inverse agonists have similarly been proposed based on animal pharmacology experiments with known histamine H$_3$ antagonists (e.g. thioperamide). These include dementia, Alzheimer's disease (Panula, P. et al., Soc. Neurosci. Abstr. 1995, 21:1977), epilepsy (Yokoyama, H. et al., Eur. J. Pharmacol. 1993, 234:129-133), narcolepsy with or without associated cataplexy, cataplexy, disorders of sleep/wake homeostasis, idiopathic somnolence, excessive daytime sleepiness (EDS), circadian rhythm disorders, sleep/fatigue disorders, fatigue, drowsiness associated with sleep apnea, sleep impairment due to perimenopausal hormonal shifts, jet lag, Parkinson's-related fatigue, multiple sclerosis (MS)-related fatigue, depression-related fatigue, chemotherapy-induced fatigue, eating disorders (Machidori, H. et al., Brain Res. 1992, 590: 180-186), motion sickness, vertigo, attention deficit hyperactivity disorders (ADHD), learning and memory (Barnes, J. C. et al., Soc. Neurosci. Abstr. 1993, 19:1813), and schizophrenia (Schlicker, E. and Marr, I., Naunyn-Schmiedeberg's Arch. Pharmacol. 1996, 353:290-294). (Also see: Stark, H. et al., Drugs Future 1996, 21(5):507-520; and Leurs, R. et al., Prog. Drug Res. 1995, 45:107-165 and references cited therein.) Histamine H$_3$ antagonists, alone or in combination with a histamine H$_1$ antagonist, are reported to be useful for the treatment of upper airway allergic response (U.S. Pat. Nos. 5,217,986; 5,352,707 and 5,869,479). Recently, a histamine H$_3$ antagonist (GT-2331) was identified and is being developed by Gliatech Inc. (Gliatech Inc. Press Release Nov. 5, 1998; Bioworld Today, Mar. 2, 1999) for the treatment of CNS disorders.

As noted, the literature related to histamine H$_3$ ligands has been comprehensively reviewed ("The Histamine H$_3$ Receptor—A Target for New Drugs", Leurs, R. and Timmerman, H., (Eds.), Elsevier, 1998). Within this reference the medicinal chemistry of histamine H$_3$ agonists and antagonists was reviewed (see Krause, M. et al., and Phillips, J. G. and Ali, S. M., respectively). The importance of an imidazole moiety containing only a single substitution in the 4-position was noted, together with the deleterious effects of additional substitution on activity. Particularly, methylation of the imidazole ring at any of the remaining unsubstituted positions was reported to strongly decrease activity. Additional publications support the hypothesis that an imidazole function is essential for high affinity histamine H$_3$ receptor ligands (see Ali, S. M. et al., J. Med. Chem. 1999, 42:903-909, and Stark, H. et al., and references cited therein). However, many imidazole-containing compounds are substrates for histamine methyl transferase, the major histamine metabolizing enzyme in humans, which leads to shortened half-lives and lower bioavailability (see Rouleau, A. et al., J. Pharmacol. Exp. Ther. 1997, 281 (3):1085-1094). In addition, imidazole-containing drugs, via their interaction with the cytochrome P$_{450}$ monooxygenase system, can participate in unfavorable biotransformations due to enzyme induction or enzyme inhibition (see: Kapetanovic, I. M. and Kupferberg, H. J., Drug Metab. Dispos. 1984, 12(5):560-564; Sheets, J. J. and Mason, J. I., Drug Metab. Dispos. 1984, 12(5):603-606; Back, D. J. and Tjia, J. F., Br. J. Pharmacol. 1985, 85:121-126; Lavrijsen, K. et al., Biochem. Pharmacol. 1986, 35(11):1867-1878; Albengres, E. et al., Drug Safety 1998, 18(2):83-97). The poor blood brain barrier penetration of earlier histamine H$_3$ receptor ligands may also be associated with the imidazole fragment (Ganellin, C. R. et al., Arch. Pharm. Pharm. Med. Chem. (Weinheim, Ger.) 1998, 331:395-404).

More recently, several publications have described histamine H$_3$ ligands that do not contain an imidazole moiety, for example: Ganellin, C. R. et al.; Walczynski, K. et al., Arch.

Pharm. Pharm. Med. Chem. (Weinheim, Ger.) 1999, 332: 389-398; Walczynski, K. et al., Farmaco 1999, 54:684-694; Linney, I. D. et al., J. Med. Chem. 2000, 43:2362-2370; Tozer, M. J. and Kalindjian, S. B., Exp. Opin. Ther. Patents 2000, 10:1045-1055; U.S. Pat. No. 5,352,707; PCT Application WO 99/42458, Aug. 26, 1999; PCT Application WO 02/076925; and European Patent Application 0978512, Feb. 9, 2000.

In addition, a more recent review of this topic was presented (Tozer, M. T. and Kalindjian, S. B. Exp. Opin. Ther. Patents 2000, 10:1045). Additional publications and patents, concerning both histamine $H_3$ agonists and antagonists, have appeared since the publication of the Leurs monograph. Most noteworthy is the development of non-imidazole histamine $H_3$ antagonists (Apodaca et al WO 02/12214; Apodaca et al WO 02/12190; Bogenstaetter et al 02/12224; Carruthers et al WO 01/74810; Chai et al WO 01/74814; Breitenbucher et al WO 01/74815; Breitenbucher et al WO 01/74813; Breitenbucher et al WO 01/74773; Bennani et al WO 02/06223; Bennani et al WO 01/66534; Schwartz et al EP 0978512 A1; Schwartz et al WO 00/06254; Linney et al J. Med. Chem. 2000, 43, 2362; and Ganellin et al Arch. Pharm. Pharm. Med. Chem. 1998, 331, 395).

The compounds of the present invention do not contain the imidazole moiety, and its inherent liabilities, and yet maintain potency at the human $H_3$ receptor as determined by receptor binding to the human histamine $H_3$ receptor (see Lovenberg, T. W. et al., Mol. Pharmacol. 1999, 55:1101-1107). Screening using the human receptor is particularly important for the identification of new therapies for the treatment of human disease. Conventional binding assays, for example, are determined using rat synaptosomes (Garbarg, M. et al., J. Pharmacol. Exp. Ther. 1992, 263(1):304-310), rat cortical membranes (West, R. E. et al., Mol. Pharmacol. 1990, 38:610-613), and guinea pig brain (Korte, A. et al., Biochem. Biophys. Res. Commun. 1990, 168(3):979-986). Only limited studies have been performed previously using human tissue but these allude to significant differences in the pharmacology of rodent and primate receptors (West, R. E. et al., Eur. J. Pharmacol. 1999, 377:233-239).

Described herein is a series of 5-membered aromatic heterocyclic compounds with the ability to modulate the activity of the histamine receptor, specifically the $H_3$ receptor, without the inherent problems associated with the presence of an imidazole moiety.

SUMMARY OF THE INVENTION

The invention features a heterocyclic compound of formula (I):

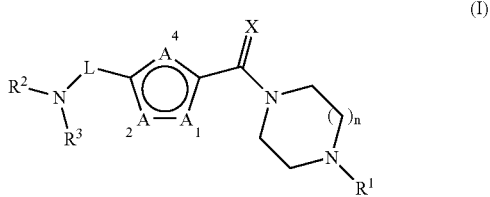

wherein
$R^1$, optionally mono- or di-substituted with $R^s$, is selected from the group consisting of —H, —$C_{1-7}$alkyl, —$C_{2-7}$alkenyl, —$C_{2-7}$alkynyl, and —$C_{3-7}$cycloalkyl;
$R^s$ is independently selected from the group consisting of —$C_{1-6}$alkyl, —$C_{2-6}$alkenyl, —$C_{3-6}$cycloalkyl, phenyl, pyridyl, furanyl, thienyl, benzyl, pyrimidinyl, pyrrolyl, halo, —OH, —$OC_{1-6}$alkyl, —$OC_{3-6}$cycloalkyl, -Ophenyl, -Obenzyl, —SH, —$SC_{1-6}$alkyl, —$SC_{3-6}$cycloalkyl, -Sphenyl, -Sbenzyl, —CN, —$NO_2$, —N($R^m$)$R^n$ (wherein $R^m$ and $R^n$ are independently H or $C_{1-4}$alkyl), —(C=O)N($R^m$)$R^n$, —(C=O)$C_{1-4}$alkyl, —$SCF_3$, —$OCF_3$, —$CF_3$, —$COOC_{1-4}$alkyl, and —COOH;
n is 1 or 2;
X is O or S;
in the A-containing ring, one of A is selected from the group consisting of —O—, —S—, —NH, or —$NC_{1-4}$alkyl; one of A is =CH—; and one of A is =CH— or =N—; provided that only one A can contain a N, and provided that the two adjacent A's are not simultaneously heteroatoms;
L is —$C_{1-4}$alkylene-;
$R^2$, optionally mono- or di-substituted with $R^q$, is independently selected from the group consisting of —H, —$C_{1-7}$alkyl, —$C_{2-7}$alkenyl, —$C_{2-7}$alkynyl, —$C_{3-7}$cycloalkyl, phenyl, benzyl, pyridinyl, pyrimidinyl, furanyl, thienyl, pyrrolyl, and a 5-, 6-, or 7-membered monocyclic non-aromatic heterocyclic ring having 1 or 2 heteroatom members selected from O, S, —N=, >NH, and >$NC_{1-4}$alkyl, having 0, 1, or 2 double bonds; and
$R^3$, optionally mono- or di-substituted with R is independently selected from the group consisting of —$C_{1-7}$alkyl, —$C_{2-7}$alkenyl, —$C_{2-7}$alkynyl, —$C_{3-7}$cycloalkyl, phenyl, benzyl, pyridinyl, pyrimidinyl, furanyl, thienyl, pyrrolyl, and a 5-, 6-, or 7-membered monocyclic non-aromatic heterocyclic ring having 1 or 2 heteroatom members selected from O, S, —N=, >NH, and >$NC_{1-4}$alkyl, having 0, 1, or 2 double bonds;
$R^q$ is independently selected from the group consisting of —$C_{1-6}$alkyl, —$C_{2-6}$alkenyl, —$C_{3-6}$cycloalkyl, phenyl, pyridyl, furanyl, thienyl, benzyl, pyrimidinyl, pyrrolyl, halo, —OH, —$OC_{1-6}$alkyl, —$OC_{3-6}$cycloalkyl, -Ophenyl, -Obenzyl, —SH, —$SC_{1-6}$alkyl, —$SC_{3-6}$cycloalkyl, -Sphenyl, -Sbenzyl, —CN, —$NO_2$, —N($R^y$)$R^z$ (wherein $R^y$ and $R^z$ are independently selected from H and $C_{1-4}$alkyl; or $R^y$ and $R^z$ may be taken together with the nitrogen of attachment to form a 5-, 6-, or 7-membered monocyclic heterocyclic ring having 1 or 2 additional heteroatom members selected from O, S, —N=, >NH, and >$NC_{1-4}$alkyl, said ring optionally substituted with halo or —$C_{1-4}$alkyl), —(C=O)N($R^y$)$R^z$, —(C=O)$C_{1-4}$alkyl, —$SCF_3$, —$OCF_3$, —$CF_3$, and —$COOC_{1-4}$alkyl, and —COOH;
or, alternatively
$R^2$ and $R^3$ may be taken together with the nitrogen of attachment to form a ring, said ring selected from the group consisting of:
  i) a 4-7 membered non-aromatic heterocyclic ring said heterocyclic ring having 0 or 1 additional heteroatom members separated from the nitrogen of attachment by at least one carbon member and selected from O, S, —N=, >NH, and >$NR^{pp}$, having 0, 1, or 2 double bonds, having 0, 1, or 2 carbon members which is a carbonyl, having 0, 1, or 2 substituents $R^p$; and
  ii) a benzo or pyrido fused 4-7 membered non-aromatic heterocyclic ring said heterocyclic ring having 0 or 1 additional heteroatom members separated from the nitrogen of attachment by at least one carbon member and selected from O, S, —N=, >NH, and >$NR^{pp}$, having 0 or 1 additional double bonds, having 0, 1, or 2 carbon members which is a carbonyl, and having 0, 1, or 2 substituents $R^p$;
$R^p$ is independently selected from the group consisting of —$C_{1-6}$alkyl, —$C_{2-6}$alkenyl, —$C_{3-6}$cycloalkyl, phenyl, pyridyl, furanyl, thienyl, benzyl, pyrimidinyl, pyrrolyl, halo, —OH, —OC$_{1-6}$alkyl, —OC$_{3-6}$cycloalkyl, -Ophenyl, -Obenzyl, —SH, —SC$_{1-6}$alkyl, —SC$_{3-6}$cycloalkyl, -Sphenyl, -Sbenzyl, —CN, —NO$_2$, —N(R$^y$)R$^z$ (wherein R$^y$ and R$^z$ are independently selected from H and C$_{1-4}$alkyl; or R$^y$ and R$^z$ may be taken together with the nitrogen of attachment to form a 5-, 6-, or 7-membered monocyclic heterocyclic ring having 1 or 2 additional heteroatom members selected from O, S, —N=, >NH, and >NC$_{1-4}$alkyl, said ring optionally substituted with halo or —C$_{1-4}$alkyl), —(C=O)N(R$^y$)R$^z$, —(C=O)C$_{1-4}$alkyl, —SCF$_3$, —OCF$_3$, —CF$_3$, —COOC$_{1-4}$alkyl, and —COOH;

R$^{pp}$ is independently selected from the group consisting of —C$_{1-6}$alkyl, —C$_{2-6}$alkenyl, —C$_{3-6}$cycloalkyl, phenyl, pyridyl, benzyl, pyrimidinyl, pyrrolyl, —(C=O)N(R$^y$)R$^z$, —(C=O)C$_{1-4}$alkyl, —COOC$_{1-4}$alkyl, and —COOC$_{1-4}$benzyl;

and enantiomers, diastereomers, hydrates, solvates and pharmaceutically acceptable salts, esters and amides thereof.

Similarly, isomeric forms of the compounds of formula (I), and of their pharmaceutically acceptable salts, esters, and amides, are encompassed within the present invention, and reference herein to one of such isomeric forms is meant to refer to at least one of such isomeric forms. One of ordinary skill in the art will recognize that compounds according to this invention may exist, for example in a single isomeric form whereas other compounds may exist in the form of a regioisomeric mixture.

The invention also features pharmaceutical compositions containing such compounds and methods of using such compositions in the treatment or prevention of disease states mediated by histamine H$_3$ receptor activity.

The invention also features a pharmaceutical composition comprising a compound of the invention and a pharmaceutically acceptable carrier; and methods of preparing or formulating such compositions. A composition of the invention may further include more than one compound of the invention, or a combination therapy (combination formulation or combination of differently formulated active agents).

The invention also provides methods of treating certain conditions and diseases, each of which methods includes administering a therapeutically effective (or jointly effective) amount of a compound or composition of the invention to a subject in need of such treatment. The disclosed compounds are useful in methods for treating or preventing neurologic disorders including sleep/wake and arousal/vigilance disorders (e.g. insomnia and jet lag), attention deficit hyperactivity disorders (ADHD), learning and memory disorders, cognitive dysfunction, migraine, neurogenic inflammation, dementia, mild cognitive impairment (pre-dementia), Alzheimer's disease, epilepsy, narcolepsy with or without associated cataplexy, cataplexy, disorders of sleep/wake homeostasis, idiopathic somnolence, excessive daytime sleepiness (EDS), circadian rhythm disorders, sleep/fatigue disorders, fatigue, drowsiness associated with sleep apnea, sleep impairment due to perimenopausal hormonal shifts, Parkinson's-related fatigue, MS-related fatigue, depression-related fatigue, chemotherapy-induced fatigue, eating disorders, obesity, motion sickness, vertigo, schizophrenia, substance abuse, bipolar disorders, manic disorders and depression, as well as other histamine H$_3$ receptor mediated disorders such as upper airway allergic response, asthma, itch, nasal congestion and allergic rhinitis in a subject in need thereof. For example, the invention features methods for preventing, inhibiting the progression of, or treating upper airway allergic response, asthma, itch, nasal congestion and allergic rhinitis.

In yet another embodiment, the disclosed compounds may be used in a combination therapy method including administering a jointly effective dose of an H$_3$ antagonist and administering a jointly effective dose of a histamine H$_1$ antagonist, such as loratidine (CLARITIN™), desloratidine (CLARINEX™), fexofenadine (ALLEGRA™) and cetirizine (ZYRTEC™), for the treatment of allergic rhinitis, nasal congestion, and allergic congestion.

In yet another embodiment, the disclosed compounds may be used in a combination therapy method, including administering a jointly effective dose of an H$_3$ antagonist and administering a jointly effective dose of a neurotransmitter re-uptake blocker, such as a selective serotonin re-uptake inhibitor (SSRI), a serotonin-norepinephrine reuptake inhibitor, a noradrenergic reuptake inhibitor, or a non-selective serotonin, dopamine or norepinephrine re-uptake inhibitor, including fluoxetine (PROZAC™), sertraline (ZOLOFT™), paroxetine (PAXIL™) and amitryptyline, for the treatment of depression, mood disorders or schizophrenia. In an alternative embodiment, the disclosed compounds may be used in a combination therapy method, including administering a jointly effective dose of an H$_3$ antagonist and administering a jointly effective dose of modafinil, for example, for the treatment of narcolepsy, excessive daytime sleepiness (EDS), Alzheimer's disease, depression, attention deficit disorders, MS-related fatigue, post-anesthesia grogginess, cognitive impairment, schizophrenia, spasticity associated with cerebral palsy, age-related memory decline, idiopathic somnolence, or jet-lag.

Additional features and advantages of the invention will become apparent from the detailed description and examples below, and the appended claims.

DETAILED DESCRIPTION

Preferably, R$^1$ is selected from the group consisting of —H, methyl, ethyl, propyl, isopropyl, butyl, isobutyl, propenyl, propargyl, cyclopropyl, cyclobutyl, cyclopentyl, hydroxyethyl, methoxyethyl, and diethylaminoethyl.

More preferably, R$^1$ is selected from the group consisting of methyl, ethyl, isopropyl, and cyclopropyl.

Even more preferably, R$^1$ is isopropyl.

Preferably, n is 1.

Preferably, X is O.

Preferably, the A-containing ring is selected from the group consisting of furan, thiophene, pyrrole, oxazole, and thiazole.

Preferably, A at the 4-position is O or S and the A's at the 1- and 2-positions are CH; A at the 2-position is S and the A's at the 1- and 4-positions are CH; A at the 1-position is N(C$_{1-4}$alkyl) and the A's at the 2- and 4-positions are CH; or A at the 2-position is S or O, A at the 4-position is N and A at the 1-position is CH.

More preferably, one of A is S or O.

More preferably, the A-containing ring is furan or thiophene.

Even more preferably, A at the 4-position is O.

Even more preferably, A at the 4-position is S.

Even more preferably, A at the 2-position is S.

Preferably, L is methylene.

Preferably, R$^2$ is independently selected from the group consisting of —H, methyl, ethyl, propyl, isopropyl, butyl, isobutyl, methoxyethyl, hydroxyethyl, piperidinylethyl, morpholinylethyl, pyridylethyl, diethylaminoethyl, propenyl, propargyl, cyclopropyl, cyclopentyl, cyclohexyl, phenyl, benzyl, pyridinyl, pyrrolyl, pyrrolidinyl, piperidinyl, morpholinyl, thiomorpholinyl, and azepanyl.

More preferably, $R^2$ is independently selected from the group consisting of —H, methyl, ethyl, propyl, isopropyl, butyl, isobutyl, methoxyethyl, cyclopropyl, piperidinylethyl, morpholinylethyl, pyridylethyl, and diethylaminoethyl.

Even more preferably, $R^2$ is independently selected from the group consisting of —H, methyl, and methoxyethyl.

Preferably, $R^3$ is independently selected from the group consisting of methyl, ethyl, propyl, isopropyl, butyl, isobutyl, methoxyethyl, hydroxyethyl, piperidinylethyl, morpholinylethyl, pyridylethyl, diethylaminoethyl, propenyl, propargyl, cyclopropyl, cyclopentyl, cyclohexyl, phenyl, benzyl, pyridinyl, pyrrolyl, pyrrolidinyl, piperidinyl, morpholinyl, thiomorpholinyl, and azepanyl.

More preferably, $R^3$ is independently selected from the group consisting of methyl, ethyl, propyl, isopropyl, butyl, isobutyl, methoxyethyl, cyclopropyl, piperidinylethyl, morpholinylethyl, pyridylethyl, and diethylaminoethyl.

Even more preferably, $R^3$ is independently selected from the group consisting of methyl and methoxyethyl.

Where $R^2$ and $R^3$ are taken together with the nitrogen of attachment to form a ring, preferably said ring is selected from the group consisting of piperidine, morpholine, thiomorpholine, piperazine, and pyrrolidine.

More preferably, $R^2$ and $R^3$ may be taken together with the nitrogen of attachment to form a ring selected from the group consisting of piperidine, morpholine, and piperazine.

In an alternative embodiment, $R^2$ and $R^3$ may be taken together with the nitrogen of attachment to form 4-fluoropiperidine.

Even more preferably, $R^2$ and $R^3$ may be taken together with the nitrogen of attachment to form a ring selected from the group consisting of piperidine and morpholine.

Preferably, $R^{pp}$ is —$C_{1-6}$alkyl.

Any of the preferred substituents described above that can be optionally further substituted with any of $R^s$, $R^q$, $R^p$, or $R^{pp}$ according to formula (I) are intended to be so optionally substituted.

It is understood that some compounds referred to herein are chiral and/or have geometric isomeric centers, for example E- and Z-isomers. The present invention encompasses all such optical isomers, including stereoisomers and racemic mixtures, diastereomers, and geometric isomers that possess the activity that characterizes the compounds of this invention. Compounds of the invention may exist as single enantiomers, mixtures of enantiomers, or racemic mixtures. In certain embodiments, the absolute configuration of a single enantiomer may be unknown. In addition, certain compounds referred to herein can exist in solvated as well as unsolvated forms. It is understood that this invention encompasses all such solvated and unsolvated forms that possess the activity that characterizes the compounds of this invention.

Compounds according to the present invention that have been modified to be detectable by some analytic technique are also within the scope of this invention. The compounds of the present invention may be labeled with radioactive elements such as $^{125}I$, $^{18}F$, $^{11}C$, $^{64}Cu$, and the like for use in imaging or for radioactive treatment of patients. An example of such compounds is an isotopically labeled compound, such as an $^{18}F$ isotopically labeled compound that may be used as a probe in detection and/or imaging techniques, such as positron emission tomography (PET) and single-photon emission computed tomography (SPECT). Preferably, compounds of the present invention labeled with $^{18}F$ or $^{11}C$ may be used as a positron emission tomography (PET) molecular probe for studying disorders mediated by the histamine $H_3$ receptor and the serotonin transporter. Another example of such compounds is an isotopically labeled compound, such as a deuterium and/or tritium labeled compound that may be used in reaction kinetic studies. The compounds described herein may be reacted with an appropriate functionalized radioactive reagents using conventional chemistry to provide radiolabeled compounds.

Pharmaceutically acceptable salts, esters, and amides include carboxylate salts (e.g., $C_{1-8}$alkyl, $C_{3-8}$cycloalkyl, aryl, $C_{2-10}$heteroaryl, or $C_{2-10}$ non-aromatic heterocyclic), amino addition salts, acid addition salts, esters, and amides that are within a reasonable benefit/risk ratio, pharmacologically effective and suitable for contact with the tissues of patients without undue toxicity, irritation, or allergic response. Representative salts for compounds of formula (I) displaying basic functionality include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. Representative addition salts for compounds of formula (I) displaying acidic functionality are those that form non-toxic base salts with such compounds. These salts may include alkali metal and alkali earth cations such as sodium, potassium, calcium, and magnesium, as well as non-toxic ammonium, quaternary ammonium, and amine cations such as tetramethyl ammonium, methylammonium, trimethylammonium, and ethylammonium. See example, S. M. Berge, et al., "Pharmaceutical Salts," J. Pharm. Sci., 1977, 66:1-19, which is incorporated herein by reference.

Representative pharmaceutically acceptable amides of the invention include those derived from ammonia, primary $C_{1-6}$ alkyl amines and secondary di($C_{1-6}$alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$alkyl primary amines, and di($C_{1-2}$alkyl)amines. Representative pharmaceutically acceptable esters of the invention include $C_{1-7}$alkyl, $C_{5-7}$cycloalkyl, phenyl, and phenyl($C_{1-6}$)alkyl esters. Preferred esters include methyl esters.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound that may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985. In addition to salts, the invention provides the esters, amides, and other protected or derivatized forms of the described compounds.

Preferred compounds of the present invention are selected from the group consisting of:

| EX | Compound Name |
|---|---|
| 1 | (4-Isopropyl-piperazin-1-yl)-(5-piperidin-1-ylmethyl-furan-2-yl)-methanone; |
| 2 | (4-Isopropyl-piperazin-1-yl)-(5-morpholin-4-ylmethyl-furan-2-yl)-methanone; |

| EX | Compound Name |
|---|---|
| 3 | (4-Isopropyl-piperazin-1-yl)-{5[(2-methoxy-ethylamino)-methyl]-furan-2-yl}-methanone; |
| 4 | (4-Isopropyl-piperazin-1-yl)-(5-piperidin-1-ylmethyl-thiophen-2-yl)-methanone; |
| 5 | (4-Isopropyl-piperazin-1-yl)-(5-morpholin-4-ylmethyl-thiophen-2-yl)-methanone; |
| 6 | (4-Isopropyl-piperazin-1-yl)-{5-[(2-methoxy-ethylamino)-methyl]-thiophen-2-yl}-methanone; |
| 7 | (4-Isopropyl-piperazin-1-yl)-(5-piperidin-1-ylmethyl-thiophen-3-yl)-methanone; |
| 8 | (4-Isopropyl-piperazin-1-yl)-(5-morpholin-4-ylmethyl-thiophen-3-yl)-methanone; |
| 9 | (4-Isopropyl-piperazin-1-yl)-(1-methyl-4-piperidin-1-ylmethyl-1H-pyrrol-2-yl)-methanone; |
| 10 | (4-Isopropyl-piperazin-1-yl)-(1-methyl-4-morpholin-4-ylmethyl-1H-pyrrol-2-yl)-methanone; |
| 11 | (4-Isopropyl-piperazin-1-yl)-(2-piperidin-1-ylmethyl-thiazol-4-yl)-methanone; |
| 12 | (4-Isopropyl-piperazin-1-yl)-(2-morpholin-4-ylmethyl-thiazol-4-yl)-methanone; |
| 13 | (4-Isopropyl-piperazin-1-yl)-{2-[(2-methoxy-ethylamino)-methyl]-thiazol-4-yl}-methanone; |
| 14 | (4-Isopropyl-piperazin-1-yl)-(2-piperidin-1-ylmethyl-oxazol-4-yl)-methanone; |
| 15 | (4-Isopropyl-piperazin-1-yl)-(2-morpholin-4-ylmethyl-oxazol-4-yl)-methanone; |
| 16 | (4-Isopropyl-piperazin-1-yl)-{2-[(2-methoxy-ethylamino)-methyl]-oxazol-4-yl}-methanone; |
| 17 | (4-Isopropyl-piperazin-1-yl)-(5-piperidin-1-ylmethyl-furan-2-yl)-methanethione; |
| 18 | [5-(4-Fluoro-piperidin-1-ylmethyl)-furan-2-yl]-(4-isopropyl-piperazin-1-yl)-methanone; and |
| 19 | [5-(4-Fluoro-piperidin-1-ylmethyl)-furan-2-yl]-(4-isopropyl-piperazin-1-yl)-methanone, fumarate salt. |

In a preferred embodiment, compounds of the present invention are selected from the group consisting of:

| EX | Compound Name |
|---|---|
| 1 | (4-Isopropyl-piperazin-1-yl)-(5-piperidin-1-ylmethyl-furan-2-yl)-methanone; |
| 4 | (4-Isopropyl-piperazin-1-yl)-(5-piperidin-1-ylmethyl-thiophen-2-yl)-methanone; |
| 5 | (4-Isopropyl-piperazin-1-yl)-(5-morpholin-4-ylmethyl-thiophen-2-yl)-methanone; |
| 6 | (4-Isopropyl-piperazin-1-yl)-{5-[(2-methoxy-ethylamino)-methyl]-thiophen-2-yl}-methanone; |
| 7 | (4-Isopropyl-piperazin-1-yl)-(5-piperidin-1-ylmethyl-thiophen-3-yl)-methanone; |
| 8 | (4-Isopropyl-piperazin-1-yl)-(5-morpholin-4-ylmethyl-thiophen-3-yl)-methanone; and |
| 9 | (4-Isopropyl-piperazin-1-yl)-(1-methyl-4-piperidin-1-ylmethyl-1H-pyrrol-2-yl)-methanone. |

The features and advantages of the invention are apparent to one of ordinary skill in the art. Based on this disclosure, including the summary, detailed description, background, examples, and claims, one of ordinary skill in the art will be able to make modifications and adaptations to various conditions and usages. Publications described herein are incorporated by reference in their entirety. Where chemical symbols are used, it is understood that they are read from left to right, and that otherwise their spatial orientation has no significance.

The compounds as described above may be made according to processes within the skill of the art and/or that are described in the schemes and examples that follow. To obtain the various compounds herein, starting materials may be employed that carry the ultimately desired substituents though the reaction scheme with or without protection as appropriate. This may be achieved by means of conventional protecting groups, such as those described in "Protective Groups in Organic Chemistry", ed. J. F. W. McOmie, Plenum Press, 1973; and T. W. Greene & P. G. M. Wuts, "Protective Groups in Organic Synthesis", 3$^{rd}$ ed., John Wiley & Sons, 1999. The protecting groups may be removed at a convenient subsequent stage using methods known from the art. Alternatively, it may be necessary to employ, in the place of the ultimately desired substituent, a suitable group that may be carried through the reaction scheme and replaced as appropriate with the desired substituent. Such compounds, precursors, or prodrugs are also within the scope of the invention.

The compounds as described above may be made according to Schemes A-D below. Persons skilled in the art will recognize that certain compounds are more advantageously produced by one scheme as compared to the other.

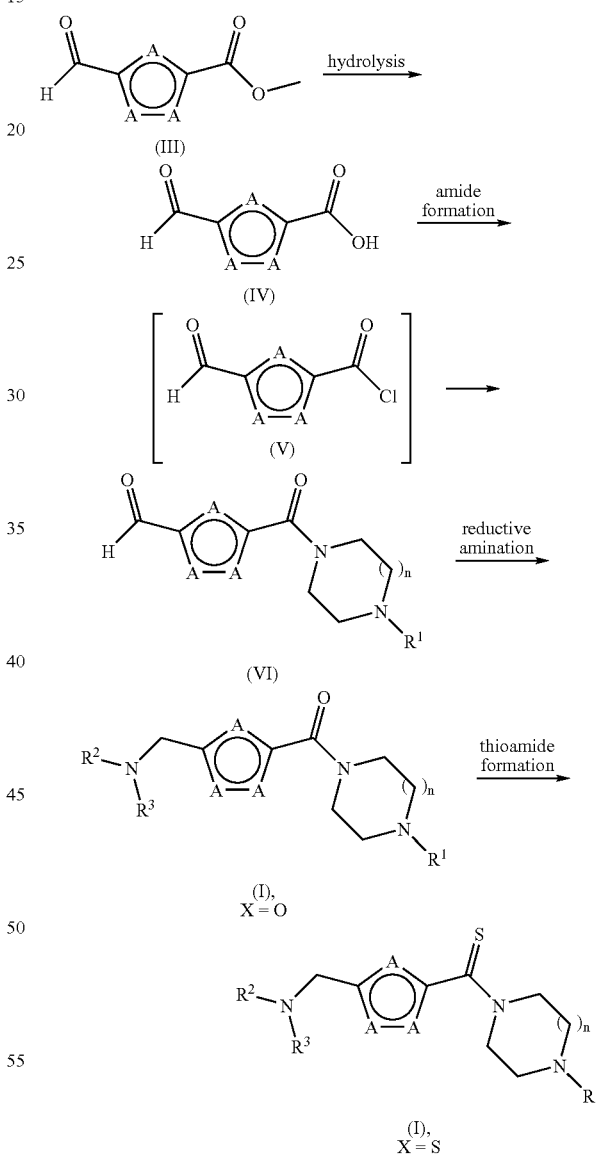

Compounds of formula (I) can be prepared as shown in Scheme A, with the following notes and additions. Commercially available esters (III) can be hydrolyzed under standard conditions (such as aqueous LiOH in dioxane) to form carboxylic acids of formula (IV). Alternatively, some acids of formula (IV) may also be obtained from commercial sources. In situ formation of acid chlorides of formula (V) can be accomplished using Vilsmeier reagent or thionyl chloride, with or without a suitable solvent such as dichloromethane.

The acid chloride is converted to the corresponding amides (VI) by treatment with a nucleophilic piperazine or azepine derivative in the presence of an acid scavenger such as TEA. The amides can also be formed directly from acids (IV) using amide-coupling methods known to those skilled in the art. The aldehyde functionality can then be reacted under conditions of reductive amination to provide compounds of formula (I). The aldehyde can be treated with a suitable primary or secondary amine, with or without the addition of an activating agent such as a protic or Lewis acid, and with an appropriate reducing agent such as sodium triacetoxyborohydride. The aldehyde may alternatively be reduced to an alcohol, converted to a leaving group such as a mesylate or chloride and displaced with an appropriate amine as shown below in Scheme B. The chloride could also be displaced with cyanide anion, and the resulting nitrile reduced to homologate the linker by one additional carbon. Alternatively, the aldehyde may be reacted using Horner-Emmons chemistry followed by hydrogenation of the double bond to introduce an alkyl chain containing an additional two carbons. The carboxamide may be converted to its corresponding thioamide by treatment with $P_2S_5$ or Lawesson's reagent.

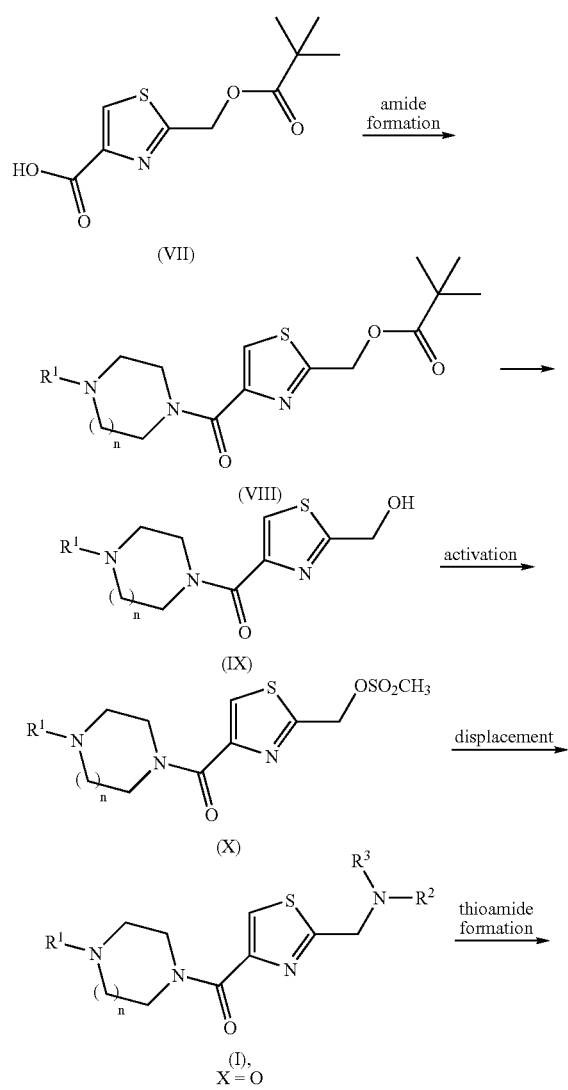

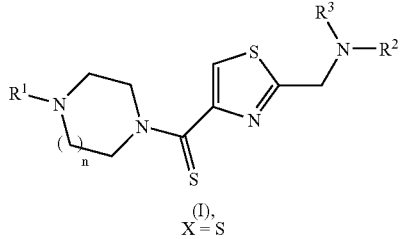

Referring to Scheme B, there are the following notes and additions. Protected hydroxy acid (VII) can be prepared as described in by Macdonald, S. J. F., et al. (J. Med. Chem. 2002, 45(18):3878-3890). Alternative protecting groups can be employed to protect the alcohol functionality. Amides of formula (VIII) are formed using standard peptide coupling conditions such as EDCl and HOBt, in a solvent such as dichloromethane. The amine coupling partner is an appropriately substituted piperazine or azepine compound. Removal of the protecting group will form alcohols of formula (IX). In the case of a tert-butyl ester, a mild base such as $K_2CO_3$, in a protic solvent such as methanol, may be employed. If other protecting groups are used, appropriate deprotection conditions will be known to one skilled in the art. The free alcohol is converted to a leaving group, such as a tosylate, mesylate, or chloride, using the appropriate sulfonyl chloride and a proton scavenger such as TEA, or thionyl or oxalyl chloride, at reduced temperature. Compounds of formula (I) are generated from the displacement of the leaving group with the desired primary or secondary amine in the presence of a suitable base such as $K_2CO_3$ or TEA.

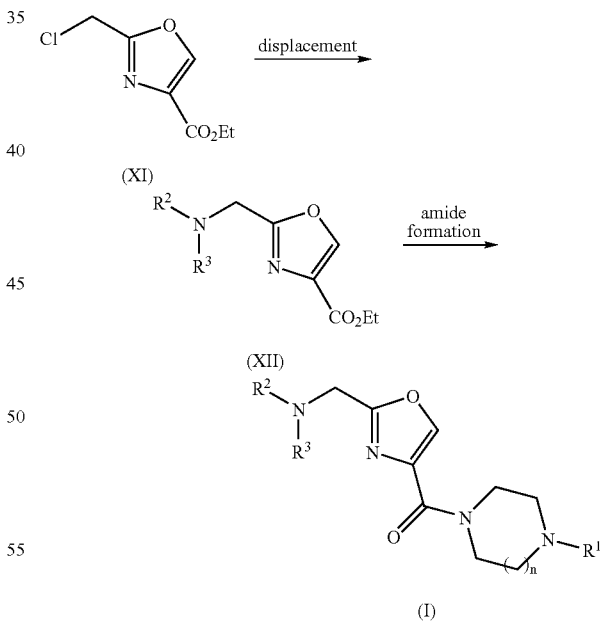

Referring to Scheme C, there are the following notes and additions. Chloromethyl oxazole (XI) is prepared in a manner analogous to that described by Cardwell, K. S., et al. (Tetrahedron Lett. 2000, 41(21):4239-4242). Displacement of the chloride is accomplished with a suitable primary or secondary amine, in a solvent such as acetonitrile, with or without heating to form esters of formula (XII). The ester functionality is then hydrolyzed under standard conditions such as LiOH in aqueous dioxane to produce the corresponding acid, which is subsequently converted into compounds of formula (I) using a piperazine or azepine derivative and standard peptide coupling conditions such as EDCl and HOBt with or without the addition of a tertiary amine base.

Compounds prepared according to the schemes described above may be obtained as single enantiomers, mixtures of enantiomers, or racemic mixtures. Where racemic (1:1) and non-racemic (not 1:1) mixtures of enantiomers are obtained, single enantiomers may be isolated using conventional separation methods known to one skilled in the art. Particularly useful separation methods may include chiral chromatography, recrystallization, resolution, diastereomeric salt formation, or derivatization into diastereomeric adducts followed by separation.

The compounds of the present invention are modulators of the histamine $H_3$ receptor, and as such, the compounds are useful in the treatment of histamine $H_3$-mediated disease states.

Compounds of the present invention may be administered in pharmaceutical compositions to treat patients (humans and other mammals) with disorders mediated by the $H_3$ receptor. The disclosed compounds, alone or in combination (with, for example, a histamine $H_1$ receptor antagonist), are useful for treating or preventing neurologic disorders including sleep/wake and arousal/vigilance disorders (e.g. insomnia and jet lag), attention deficit hyperactivity disorders (ADHD), learning and memory disorders, cognitive dysfunction, migraine, neurogenic inflammation, dementia, mild cognitive impairment (pre-dementia), Alzheimer's disease, epilepsy, narcolepsy with or without associated cataplexy, cataplexy, disorders of sleep/wake homeostasis, idiopathic somnolence, excessive daytime sleepiness (EDS), circadian rhythm disorders, sleep/fatigue disorders, fatigue, drowsiness associated with sleep apnea, sleep impairment due to perimenopausal hormonal shifts, Parkinson's-related fatigue, MS-related fatigue, depression-related fatigue, chemotherapy-induced fatigue, eating disorders, obesity, motion sickness, vertigo, schizophrenia, substance abuse, bipolar disorders, manic disorders and depression, as well as other histamine $H_3$ receptor mediated disorders such as upper airway allergic response, asthma, itch, nasal congestion and allergic rhinitis in a subject in need thereof. Excessive daytime sleepiness (EDS) may occur with or without associated sleep apnea, shift work, fibromyalgia, MS, and the like.

The present invention also provides pharmaceutical compositions comprising one or more compounds of this invention in association with a pharmaceutically acceptable carrier and optionally additional pharmaceutical agents such as $H_1$ antagonists, SSRIs, or modafinil. The pharmaceutical compositions can be prepared using conventional pharmaceutical excipients and compounding techniques known to those skilled in the art of preparing dosage forms. It is anticipated that the compounds of the invention can be administered by oral, parenteral, rectal, topical, or ocular routes, or by inhalation. Preparations may also be designed to give slow release of the active ingredient. The preparation may be in the form of tablets, capsules, sachets, vials, powders, granules, lozenges, powders for reconstitution, liquid preparations, or suppositories. Preferably, compounds may be administered by intravenous infusion or topical administration, but more preferably by oral administration.

For oral administration, the compounds of the invention can be provided in the form of tablets or capsules, or as a solution, emulsion, or suspension. Tablets for oral use may include the active ingredient mixed with pharmaceutically acceptable excipients such as inert diluents, disintegrating agents, binding agents, lubricating agents, sweetening agents, flavoring agents, coloring agents and preservatives agents. Suitable inert fillers include sodium and calcium carbonate, sodium and calcium phosphate, lactose, starch, sugar, glucose, methyl cellulose, magnesium stearate, mannitol, sorbitol, and the like; typical liquid oral excipients include ethanol, glycerol, water and the like. Starch, polyvinyl-pyrrolidone, sodium starch glycolate, microcrystalline cellulose, and alginic acid are suitable disintegrating agents. Binding agents may include starch and gelatin. The lubricating agent, if present, will generally be magnesium stearate, stearic acid or talc. If desired, the tablets may be coated with a material such as glyceryl monostearate or glyceryl distearate to delay absorption in the gastrointestinal tract, or may be coated with an enteric coating. Capsules for oral use include hard gelatin capsules in which the active ingredient is mixed with a solid, semi-solid, or liquid diluent, and soft gelatin capsules wherein the active ingredient is mixed with water, an oil such as peanut oil or olive oil, liquid paraffin, a mixture of mono and di-glycerides of short chain fatty acids, polyethylene glycol 400, or propylene glycol.

Liquids for oral administration may be suspensions, solutions, emulsions or syrups or may be presented as a dry product for reconstitution with water or other suitable vehicles before use. Compositions of such liquid may contain pharmaceutically-acceptable excipients such as suspending agents (for example, sorbitol, methyl cellulose, sodium alginate, gelatin, hydroxyethylcellulose, carboxymethylcellulose, aluminium stearate gel and the like); non-aqueous vehicles, which include oils (for example, almond oil or fractionated coconut oil), propylene glycol, ethyl alcohol or water; preservatives (for example, methyl or propyl p-hydroxybenzoate or sorbic acid); wetting agents such as lecithin; and, if needed, flavoring or coloring agents.

The compounds of this invention may also be administered by non-oral routes. The compositions may be formulated for rectal administration as a suppository. For parenteral use, including intravenous, intramuscular, intraperitoneal, or subcutaneous routes, the compounds of the invention will generally be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit dose form such as ampules or disposable injection devices, in multi-dose forms such as vials from which the appropriate dose may be withdrawn, or in a solid form or pre-concentrate that can be used to prepare an injectable formulation. Another mode of administration of the compounds of the invention may utilize a patch formulation to affect transdermal delivery. The compounds of this invention may also be administered by inhalation, via the nasal or oral routes using a spray formulation consisting of the compound of the invention and a suitable carrier.

Effective doses of the compounds of the present invention may be ascertained by conventional methods. The specific dosage level required for any particular patient will depend on a number of factors, including severity of the condition being treated, the route of administration, and the weight of the patient. In general, however, it is anticipated that the daily dose (whether administered as a single dose or as divided doses) will be in the range 0.01 to 1000 mg per day, more usually from 1 to 500 mg per day, and most usually from 10 to 200 mg per day. Expressed as dosage per unit body weight, a typical dose will be expected to be between 0.0001 mg/kg and 15 mg/kg, especially between 0.01 mg/kg and 7 mg/kg, and most especially between 0.15 mg/kg and 2.5 mg/kg.

Preferably, oral doses range from about 0.05 to 200 mg/kg, daily, taken in 1 to 4 separate doses. Some compounds of the invention may be orally dosed in the range of about 0.05 to about 50 mg/kg daily, others may be dosed at 0.05 to about 20 mg/kg daily, while still others may be dosed at 0.1 to about 10 mg/kg daily. Infusion doses can range from about 1 to 1000 μg/kg/min of inhibitor, admixed with a pharmaceutical carrier over a period ranging from several minutes to several days. For topical administration compounds of the present invention may be mixed with a pharmaceutical carrier at a concentration of about 0.1% to about 10% of drug to vehicle.

The disclosed compounds are useful in combination with other therapeutic agents, including $H_1$ receptor antagonists, $H_2$ receptor antagonists, and neurotransmitter modulators such as SSRIs, serotonin-norepinephrine reuptake inhibitors, noradrenergic reuptake inhibitors, non-selective serotonin reuptake inhibitors (NSSRIs), or other neuroactive agents such as modafinil.

Methods are known in the art for determining effective doses for therapeutic and prophylactic purposes for the disclosed pharmaceutical compositions or the disclosed drug combinations, whether or not formulated in the same composition. For therapeutic purposes, the term "jointly effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "jointly effective amount" refers to that amount of each active compound or pharmaceutical agent, alone or in combination, that inhibits in a subject the onset or progression of a disorder as being sought by a researcher, veterinarian, medical doctor or other clinician, the delaying of which disorder is mediated, at least in part, by the modulation of one or more histamine receptors. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both drugs are administered in an amount that is sub-therapeutic or sub-prophylactic if administered alone, but are therapeutic or prophylactic when administered together. Combinations of three or more drugs are analogously possible. Methods of combination therapy include co-administration of a single formulation containing all active agents; essentially contemporaneous administration of more than one formulation; and administration of two or more active agents separately formulated.

EXAMPLES

In order to illustrate the invention, the following examples are included. These examples do not limit the invention. They are only meant to suggest a method of practicing the invention. Those skilled in the art may find other methods of practicing the invention, which are obvious to them. However, those methods are deemed to be within the scope of this invention.

Protocol for Preparative Reversed-Phase HPLC

Gilson® instrument  
Column: YMC-Pack ODS-A, 5 μm, 75×30 mm  
Flow rate: 10 mL/min  
Detection: λ=220 & 254 nm  
Gradient (acetonitrile/water, 0.05% trifluoroacetic acid)

| 1) | 0.0 min | 20% acetonitrile/80% water |
| 2) | 20.0 min | 99% acetonitrile/1% water |

Protocol for HPLC (Reversed-Phase)

Hewlett Packard Series 1100  
Column: Agilent ZORBAX® C8, 5 μm, 4.6×150 mm  
Flow rate: 1 mL/min  
Detection: λ=220 & 254 nm  
Gradient (acetonitrile/water, 0.05% trifluoroacetic acid)

| 1) | 0.0 min | 1% acetonitrile/99% water |
| 2) | 8.0 min | 99% acetonitrile/1% water |

Mass spectra were obtained on an Agilent series 1100 MSD using ESI ionization (ESI) in either positive or negative modes as indicated.

NMR spectra were obtained on either a Bruker model DPX400 (400 MHz) or DPX500 (500 MHz) spectrometer. The format of the $^1$H NMR data below is: chemical shift in ppm down field of the tetramethylsilane reference (multiplicity, coupling constant J in Hz, integration).

Example 1

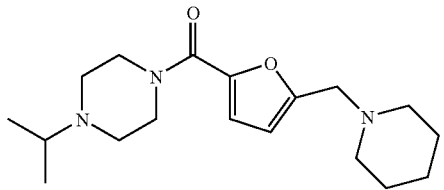

(4-Isopropyl-piperazin-1-yl)-(5-piperidin-1-ylmethyl-furan-2-yl)-methanone.

Step A. 5-(4-Isopropyl-piperazine-1-carbonyl)-furan-2-carbaldehyde. Vilsmeier reagent [(chloromethylene)dimethylammonium chloride, 0.820 g, 6.43 mmol] was suspended in DCM (30 mL) under nitrogen with stirring and cooled to 0° C. To this suspension was added 5-formyl-2-furancarboxylic acid (0.900 g, 6.43 mmol) and the combined mixture was stirred at 0° C. for 30 min. The mixture was warmed to rt, stirred for another 1.5 h, and filtered. The filtrate (containing 5-formyl-furan-2-carbonyl chloride) was set aside and maintained at 0° C. In a second flask, 1-isopropyl-piperizine dihydrochloride (1.28 g, 6.37 mmol) in DCM (15 mL) was cooled to 0° C. The solution was treated with TEA (2.250 g, 22.30 mmol) slowly and then was warmed to rt and stirred for 30 min. The reaction mixture was filtered and the filtrate was cooled to 0° C. This second filtrate was then treated dropwise with the previously prepared solution of 5-formyl-furan-2-carbonyl chloride at 0° C. The combined mixture was stirred at 0° C. for 30 min and then at rt for 1 h. The reaction mixture was cooled to 0° C. and filtered, and the filtrate was washed with H$_2$O (2×15 mL), 0.5 N NaOH (1×15 mL), and satd. aq. NaCl (1×15 mL). The organic layer was separated, dried over anhydrous Na$_2$SO$_4$, filtered, and concentrated to yield the desired product (1.40 g, 87%).

Step B. (4-Isopropyl-piperazin-1-yl)-(5-piperidin-1-ylmethyl-furan-2-yl)-methanone. A mixture of 5-(4-isopropyl-piperazine-1-carbonyl)-furan-2-carbaldehyde (0.15 g, 0.60 mmole), piperidine (0.058 mL, 0.59 mmol) and NaB(OAc)$_3$H (0.19 g, 0.90 mmol) was stirred under nitrogen in DCM (6 mL) overnight. The reaction mixture was quenched with 1 M NaOH and stirred at rt for 30 min. The mixture was diluted with H$_2$O and extracted with DCM (3×20 mL). The combined organic extracts were washed with H$_2$O, dried over anhydrous Na$_2$SO$_4$, filtered, and concentrated (0.18 g, 95%). The crude material was purified on silica gel column using 0-5% 2 M NH$_3$ in MeOH/DCM to yield the title compound (0.095 g, 50%). MS (ESI): exact mass calcd. for C$_{18}$H$_{29}$N$_3$O$_2$, 319.23; m/z found, 320.5 [M+H]$^+$. $^1$H NMR (500 MHz, CDCl$_3$): 7.13 (d, J=3.6, 1H), 6.81 (d, J=3.6, 1H), 3.76-3.71 (m, 4H), 3.65 (s, 2H), 2.74-2.68 (m, 1H), 2.56-2.50 (m, 4H), 2.45-2.36 (br s, 4H), 1.60-1.53 (m, 4H), 1.44-1.37 (m, 2H), 1.04 (d, J=6.6, 6H).

Example 2

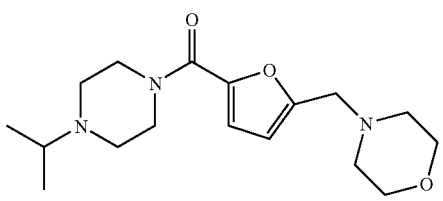

(4-Isopropyl-piperazin-1-yl)-(5-morpholin-4-ylmethyl-furan-2-yl)-methanone.

The title compound was prepared in a manner similar to that described in Example 1, Step B. MS (ESI): exact mass calcd. for C$_{17}$H$_{27}$N$_3$O$_3$, 321.21; m/z found, 322.5 [M+H]$^+$. $^1$H NMR (500 MHz, CDCl$_3$): 6.89 (d, J=3.3, 1H), 6.30 (d, J=3.3, 1H), 3.90-3.76 (br m, 4H), 3.7 (t, J=4.6, 4H), 3.58 (s, 2H), 2.82-2.72 (br s, 1H), 2.65-2.55 (br s, 4H), 2.50-2.46 (m, 4H), 1.05 (d, J=6.3, 6H).

Example 3

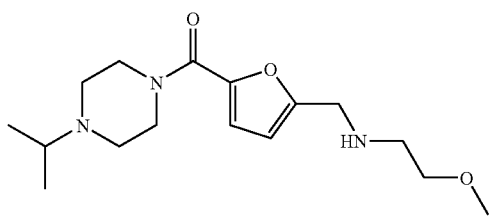

(4-Isopropyl-piperazin-1-yl)-{5-[(2-methoxy-ethylamino)-methyl]-furan-2-yl}-methanone.

The title compound was prepared in a manner similar to that described in Example 1, Step B. MS (ESI): exact mass calcd. for C$_{16}$H$_{27}$N$_3$O$_3$, 309.21; m/z found, 310.5 [M+H]$^+$. $^1$H NMR (500 MHz, CDCl$_3$): 6.84-6.79 (m, 1H), 6.25-6.20 (m, 1H), 3.83-3.66 (m, 6H), 3.49-3.24 (m, 5H), 2.79-2.60 (m, 2H), 2.55-2.45 (m, 4H), 2.37-2.20 (m, 2H), 1.00 (d, J=6.6, 6H).

Example 4

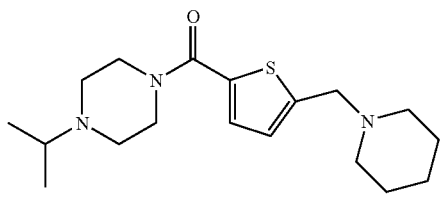

(4-Isopropyl-piperazin-1-yl)-(5-piperidin-1-ylmethyl-thiophen-2-yl)-methanone.

Step A. 5-(4-Isopropyl-piperazine-1-carbonyl)-thiophene-2-carbaldehyde. The title compound was prepared in a manner similar to that described in Example 1, Step A.

Step B. (4-Isopropyl-piperazin-1-yl)-(5-piperidin-1-ylmethyl-thiophen-2-yl)-methanone. The title compound was prepared in a manner similar to that described in Example 1, Step B. MS (ESI): exact mass calcd. for C$_{18}$H$_{29}$N$_3$OS, 335.20; m/z found, 336.5 [M+H]$^+$. $^1$H NMR (500 MHz, CDCl$_3$): 6.87 (d, J=3.3, 1H), 6.25 (d, J=3.3, 1H), 3.83-3.71 (br s, 4H), 3.54 (br s, 2H), 2.74-2.67 (m, 1H), 2.60-2.50 (m, 4H), 2.47-2.37 (m, 4H), 1.63-1.50 (m, 4H), 1.43-1.35 (m, 2H), 1.06 (d, J=6.6, 6H).

Example 5

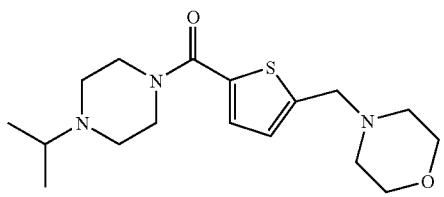

(4-Isopropyl-piperazin-1-yl)-(5-morpholin-4-ylmethyl-thiophen-2-yl)-methanone.

The title compound was prepared in a manner similar to that described in Example 1, Step B. MS (ESI): exact mass calcd. for C$_{17}$H$_{27}$N$_3$O$_2$S, 337.18; m/z found, 338.5 [M+H]$^+$. $^1$H NMR (500 MHz, CDCl$_3$): 7.13 (d, J=3.6, 1H), 6.83 (d, J=3.6, 1H), 3.78-3.73 (m, 4H), 3.70 (t, J=4.9, 4H), 3.68-3.65 (m, 2H), 2.78-2.70 (m, 1H), 2.58-2.53 (m, 4H), 2.51-2.45 (m, 4H), 1.05 (d, J=6.6, 6H).

Example 6

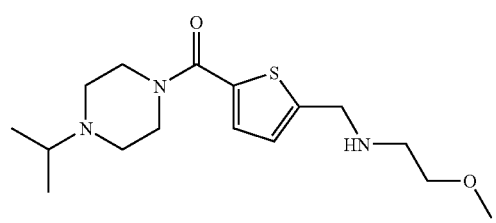

(4-Isopropyl-piperazin-1-yl)-{5-[(2-methoxy-ethylamino)-methyl]-thiophen-2-yl}-methanone.

The title compound was prepared in a manner similar to that described in Example 1, Step B. MS (ESI): exact mass calcd. for C$_{16}$H$_{27}$N$_3$O$_2$S, 325.18; m/z found, 326.4 [M+H]$^+$. $^1$H NMR (500 MHz, CDCl$_3$): 7.15 (d, J=3.6, 1H), 6.86 (d, J=3.6, 1H), 4.00 (s, 2H), 3.81-3.73 (m, 4H), 3.52-3.48 (m, 2H), 3.35 (s, 3H), 2.82 (t, J=5.2, 2H), 2.80-2.70 (m, 1H), 2.60-2.52 (m, 4H).

Example 7

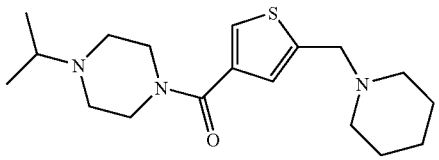

(4-Isopropyl-piperazin-1-yl)-(5-piperidin-1-ylmethyl-thiophen-3-yl)-methanone.

Step A. 4-(4-Isopropyl-piperazine-1-carbonyl)-thiophene-2-carbaldehyde. The title compound was prepared in a manner similar to that described in Example 1, Step A.

Step B. (4-Isopropyl-piperazin-1-yl)-(5-piperidin-1-ylmethyl-thiophen-3-yl)-methanone. The title compound was prepared in a manner similar to that described in Example 1, Step B, with the addition of acetic acid (1 eq.) to the reaction. MS (ESI): exact mass calcd. for $C_{18}H_{29}N_3OS$, 335.20; m/z found, 336.4 [M+H]$^+$. $^1$H NMR (500 MHz, CDCl$_3$): 7.40-7.36 (m, 1H), 7.00-6.96 (m, 1H), 3.70-3.65 (br s, 2H), 2.78-2.70 (m, 1H), 2.60-2.39 (m, 8H), 1.65-1.55 (m, 8H), 1.47-1.39 (m, 2H), 1.06 (d, J=6.6, 6H).

Example 8

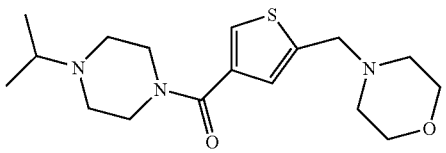

(4-Isopropyl-piperazin-1-yl)-(5-morpholin-4-ylmethyl-thiophen-3-yl)-methanone.

The title compound was prepared in a manner similar to that described in Example 1, Step B, with the addition of acetic acid (1 eq.) to the reaction. MS (ESI): exact mass calcd. for $C_{17}H_{27}N_3O_2S$, 337.18; m/z found, 338.3 [M+H]$^+$. $^1$H NMR (500 MHz, CDCl$_3$): 7.38 (d, J=1.4, 1H), 6.99-6.98 (m, 1H), 3.78-3.58 (m, 10H), 2.80-2.66 (m, 1H), 2.58-2.43 (m, 8H), 1.05 (d, 6.3, 6H).

Example 9

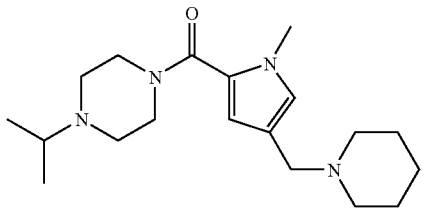

(4-Isopropyl-piperazin-1-yl)-(1-methyl-4-piperidin-1-ylmethyl-1H-pyrrol-2-yl)-methanone.

Step A. 4-Formyl-1-methyl-1H-pyrrole-2-carboxylic acid. Methyl-4-formyl-1-methyl-1H-pyrrole-2-carboxylate (1.00 g, 5.98 mmol) was dissolved in dioxane (10 mL) and 1 M aq. LiOH (6 mL) was added at rt. After 18 h, the reaction mixture was concentrated to obtain the crude acid as the lithium salt, which was carried forward to the next step.

Step B. 5-(4-Isopropyl-piperazine-1-carbonyl)-1-methyl-1H-pyrrole-3-carbaldehyde. 4-Formyl-1-methyl-1H-pyrrole-2-carboxylic acid, lithium salt, (1.08 g.) was diluted with thionyl chloride (20 mL) and heated at reflux under nitrogen for 1.5 h. The reaction mixture was carefully concentrated. The residue was co-evaporated with toluene (3×) to remove residual HCl, and then was kept under vacuum for 2 h. Separately, a solution of 1-isopropyl-piperazine dihydrochloride (1.21 g, 6.00 mmol) in DCM (50 mL) was cooled to 0-5° C. TEA (2.23 mL, 24.0 mmol) was added slowly, followed by the above acid chloride solution in DCM (50 mL). The resulting mixture was allowed to stir overnight at rt. The mixture was concentrated to yield the crude product (3.78 g), which was purified on silica gel column using 2-6% 2 M NH$_3$ in MeOH/DCM to yield the title compound (0.20 g).

Step C. (4-Isopropyl-yl)-(1-methyl-4-piperidin-1-ylmethyl-1H-pyrrol-2-yl)-methanone. The title compound was prepared in a manner similar to that described in Example 1, Step B. MS (ESI): exact mass calcd. for $C_{19}H_{32}N_4O$, 332.26; m/z found, 333.5 [M+H]$^+$. $^1$H NMR (500 MHz, CDCl$_3$): 6.58 (d, J=1.6, 1H), 6.24 (d, J=1.6, 1H), 3.76-3.70 (m, 7H), 3.32 (s, 2H), 2.75-2.66 (m, 1H), 2.53-2.50 (m, 4H), 2.41-2.27 (m, 4H), 1.59-1.51 (m, 4H), 1.43-1.35 (m, 2H), 1.04 (d, J=6.6, 6H).

Example 10

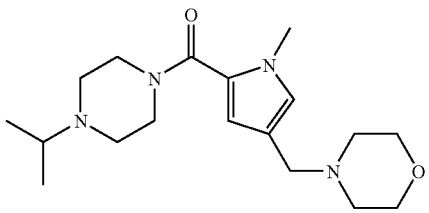

(4-Isopropyl-piperazin-1-yl)-(1-methyl-4-morpholin-4-ylmethyl-1H-pyrrol-2-yl)-methanone.

The title compound was prepared in a manner similar to that described in Example 9. MS (ESI): exact mass calcd. for $C_{18}H_{30}N_4O_2$, 334.24; m/z found, 335.5 [M+H]$^+$. $^1$H NMR (500 MHz, CDCl$_3$): 6.59 (d, J=1.6, 1H), 6.24 (d, J=1.9, 1H), 3.75-3.70 (m, 7H), 3.68 (t, J=4.7, 4H), 3.33 (s, 2H), 2.74-2.66 (m, 1H), 2.52 (t, J=4.9, 4H), 2.44-2.38 (m, 4H), 1.04 (d, J=6.6, 6H).

Example 11

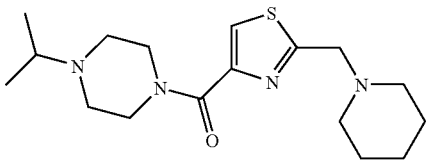

(4-Isopropyl-piperazin-1-yl)-(2-piperidin-1-ylmethyl-thiazol-4-yl)-methanone.

Step A. 2-(2,2-Dimethyl-propionyloxymethyl)-thiazole-4-carboxylic acid. A solution of 2-(tert-butylcarbonyloxy)thioacetamide (4.25 g, 24.2 mmol), bromopyruvic acid (4.60 g, 27.5 mmol), and 4 Å activated molecular sieves (27.0 g) in EtOH (250 mL) was heated at reflux for 15 h. The mixture was cooled to rt, filtered carefully, and washed with EtOH (3×50 mL). The filtrate and the washings were combined and concentrated to yield a light yellow crude solid (6.42 g), which was carried on to the next step without purification. MS (ESI): exact mass calcd. for $C_{10}H_{13}NO_4S$, 243.06; m/z found, 267.3 [M+Na]$^+$.

Step B. 2,2-Dimethyl-Propionic acid 4-(4-isopropyl-piperazine-1-carbonyl)-thiazol-2-ylmethyl ester. The crude product from Step A (6.42 g, 24.2 mmol), 1-isopropyl-piperazine dihydrochloride (5.36 g., 26.68 mmol) and 1-hydroxybenzotriazole (4.915 g., 36.38 mmol) were dissolved into a mixture of N-methylmorpholine (14.72 g., 101.20 mmol) and DCM (120 mL). The mixture was stirred for 30 min under nitrogen. 1-(3-Dimethylaminopropyl)-3-ethylcarbodiimide hydrochloride (6.97 g, 36.4 mmol) was added, and the reaction mixture was stirred for 18 h at rt. The reaction was quenched by the addition of 1 M NaOH (25 mL), and was stirred for 1 h. The mixture was diluted with water and extracted with DCM (3×60 mL). The combined organic extracts were washed with $H_2O$, dried over $Na_2SO_4$, filtered, and concentrated to yield dark brown crude oil (6.2 g). The crude product was purified on silica gel column using 30-50% acetone-DCM to give the title compound as a brown oil (3.9 g, 46%). $^1$H NMR (500 MHz, CDCl$_3$): 7.89 (s, 1H), 5.38 (s, 2H), 3.90-3.84 (m, 2H), 3.81-3.75 (m, 2H), 2.75-2.69 (m, 1H), 2.62-2.50 (m, 4H), 1.27-1.23 (s, 9H), 1.05 (d, J=6.3, 6H).

Step C. (2-Hydroxymethyl-thiazol-4-yl)-(4-isopropyl-piperazin-1-yl)-methanone. A mixture of 2,2-dimethyl-propionic acid 4-(4-isopropyl-piperazine-1-carbonyl)-thiazol-2-ylmethyl ester (3.85 g, 10.8 mmol), potassium carbonate (3.06 g., 21.7 mmol), MeOH (130 mL), and $H_2O$ (50 mL) was heated at reflux for 12 h. The reaction mixture was cooled to rt and extracted with DCM (8×50 mL). The combined organic extracts were dried over $Na_2SO_4$ and concentrated to yield a yellowish solid (2.14 g, 73.3%). MS (ESI): exact mass calcd. for $C_{12}H_{19}N_3O_2S$, 269.12; m/z found, 270.4 [M+H]$^+$.

Step D. Methanesulfonic acid 4-(4-isopropyl-piperazine-1-carbonyl)-thiazol-2-ylmethyl ester. (2-Hydroxymethyl-thiazol-4-yl)-(4-isopropyl-piperazin-1-yl)-methanone (0.95 g, 3.5 mmol) and TEA (0.542 mL, 3.89 mmol) were suspended in DCM (50 mL). The suspension was cooled to 0° C. and methanesulfonyl chloride (0.3 mL) was added dropwise. The mixture was stirred at 0° C. for 30 min, then warmed to rt and stirred for 2 h. The mixture was concentrated at rt to yield the title compound (0.50 g, 41%). The crude mesylate was carried forward to the next step. MS (ESI): exact mass calcd. for $C_{14}H_{22}N_2O_4S_2$, 347.10; m/z found, 348.5 [M+H]$^+$.

Step E. (4-Isopropyl-piperazin-1-yl)-(2-piperidin-1-ylmethyl-thiazol-4-yl)-methanone. A mixture of methanesulfonic acid 4-(4-isopropyl-piperazine-1-carbonyl)-thiazol-2-ylmethyl ester (0.052 g, 0.14 mmol), anhydrous potassium carbonate (0.054 g., 0.43 mmol), and piperidine (0.016 mL, 0.16 mmol) in anhydrous acetonitrile (4 mL) was stirred at rt for 18 h. The reaction mixture was diluted with $H_2O$ and extracted with DCM (4×15 mL). The combined organic extracts were dried over $Na_2SO_4$, filtered, and concentrated to yield the crude product (0.045 g). The crude material was purified on silica gel column using 0-5% 2 M $NH_3$ in MeOH/DCM to give the title compound (0.03 g, 62%). MS (ESI): exact mass calcd. for $C_{17}H_{28}N_4OS$, 336.20; m/z found, 337.5 [M+H]$^+$. $^1$H NMR (500 MHz, CDCl$_3$): 7.80 (s, 1H), 3.90-3.74 (m, 4H), 2.77-2.67 (m, 1H), 2.63-2.47 (m, 8H), 1.73-1.57 (m, 6H), 1.50-1.41 (m, 2H), 1.05 (d, J=6.6, 6H).

Example 12

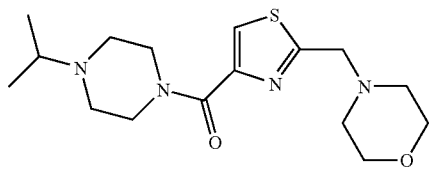

(4-Isopropyl-piperazin-1-yl)-(2-morpholin-4-ylmethyl-thiazol-4-yl)-methanone.

The title compound was prepared in a manner similar to that described in Example 11, Step E. MS (ESI): exact mass calcd. for $C_{16}H_{26}N_4O_2S$, 338.18; m/z found, 339.4 [M+H]$^+$. $^1$H NMR (500 MHz, CDCl$_3$): 7.80 (s, 1H), 3.84-3.80 (m, 4H), 3.78-3.74 (m, 4H), 3.72 (t, J=4.7, 4H), 2.72-2.66 (m, 1H), 2.58 (t, J=4.7, 6H), 2.52-2.47 (m, 2H), 1.02 (d, J=6.6, 6H).

Example 13

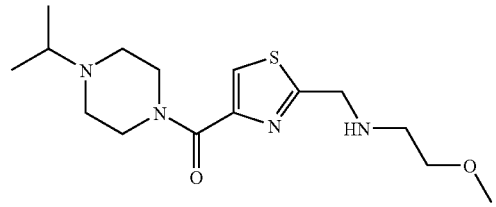

(4-Isopropyl-piperazin-1-yl)-{2-[(2-methoxy-ethylamino)-methyl]-thiazol-4-yl}-methanone.

The title compound was prepared in a manner similar to that described in Example 11, Step E. MS (ESI): exact mass calcd. for $C_{15}H_{26}N_4O_2S$, 326.18; m/z found, 327.4 [M+H]$^+$. $^1$H NMR (500 MHz, CDCl$_3$): 7.78 (s, 1H), 4.12 (s, 2H), 3.89-3.73 (m, 4H), 3.52-3.49 (m, 2H), 3.36 (s, 3H), 2.88-2.85 (m, 2H), 2.74-2.68 (m, 1H), 2.62-2.45 (m, 4H), 1.04 (d, J=6.6, 6H).

Example 14

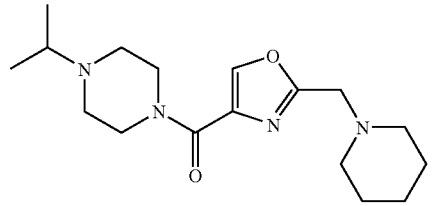

(4-Isopropyl-piperazin-1-yl)-(2-piperidin-1-ylmethyl-oxazol-4-yl)-methanone.

Step A. 2-Chloromethyl-oxazole-4-carboxylic acid ethyl ester. Sodium methoxide (25% w/w solution in MeOH, 0.07 mL, 0.30 mmol) was added to a mixture of DCM (21.5 mL) and MeOH (2.40 mL) and the mixture was cooled to −5° C. Dichloroacetonitrile was added (3.25 g., 29.6 mmol) dropwise over 45 min, maintaining the temperature below 0° C., and the mixture was then stirred for 60 min at 0° C. Serine ethyl ester hydrochloride (5.00 g, 29.5 mmol) was added and the mixture was stirred overnight at 20° C. The slurry was diluted with DCM and $H_2O$ (12 mL), and was extracted with DCM (20-25 mL). The combined organic extracts were concentrated at atmospheric pressure to 15 mL. N,N-Diisopropylethylamine (7.72 mL, 44.3 mmol) was added and the mixture was heated at 50° C. for 5 h. The mixture was cooled to rt and was stirred overnight. The mixture was diluted with DCM (19 mL) and cooled to 5° C. To this mixture was cautiously added 2 M HCl (21.6 mL). The organic layer was separated, washed with H$_2$O (12 mL), and concentrated to 27 mL. This solution containing the title compound was carried forward for alkylation. The solution was divided into 3 equal parts and it was assumed that each part (9 mL) contained 9.80 mmol of the crude product.

Step B. 2-Piperidin-1-ylmethyl-oxazole-4-carboxylic acid ethyl ester. A solution of 2-chloromethyl-oxazole-4-carboxylic acid ethyl ester (estimated 9.0 mL, 9.8 mmol) was cooled to 15° C. and piperidine (1.92 mL, 19.4 mmol) was added slowly over 10 min. The mixture was heated at reflux for 30 min and then cooled to −5° C. and filtered. The filtrate was concentrated at rt under vacuum (40 mm Hg). The resulting oily crude product (approximately 2.38 g) was carried on to the saponification step.

Step C. 2-Piperidin-1-ylmethyl-oxazole-4-carboxylic acid. To a rt solution of the crude ester from Step B (est. 2.38 g) in dioxane (50 mL) was added 1 M aq. LiOH (11 mL). After 18 h, the reaction mixture was concentrated on a rotary evaporator at low temperature to yield the crude acid as its lithium salt (1.73 g). The crude product was carried to the next step. MS (ESI): exact mass calcd. for $C_{10}H_{14}N_2O_3$, 210.10; m/z found, 211.4 [M+H]$^+$.

Step D. (4-Isopropyl-piperazin-1-yl)-(2-piperidin-1-ylmethyl-oxazol-4-yl)-methanone. A solution of 2-piperidin-1-ylmethyl-oxazole-4-carboxylic acid, lithium salt (0.400 g, 1.85 mmol), 1-isopropyl-piperazine dihydrochloride (0.409 g., 2.03 mmol), 1-hydroxybenzotriazole (0.300 g., 2.22 mmol), and N-methylmorpholine (1.22 mL, 11.1 mmol) in anhydrous DCM (18 mL) was stirred for 1 h. 1-(3-Dimethylaminopropyl)-3-ethylcarbodiimide hydrochloride (0.426 g., 2.22 mmol) was added, and the reaction mixture was stirred at rt for 18 h. The reaction was quenched by the addition of 1 M NaOH (20 mL) was stirred for 1 h. The resulting mixture was extracted with DCM (3×30 mL). The combined organic extracts were washed with H$_2$O, dried over Na$_2$SO$_4$, filtered, and concentrated to yield the crude product (0.700 g). The crude product was purified on silica gel column using 0-5% 2 M NH$_3$ in MeOH/DCM to provide the title compound (0.345 g, 58.2%). MS (ESI): exact mass calcd. for $C_{17}H_{28}N_4O_2$, 320.22; m/z found, 321.5 [M+H]$^+$. $^1$H NMR (500 MHz, CDCl$_3$): 8.10 (s, 1H), 4.09-4.00 (m, 2H), 3.77-3.70 (m, 2H), 3.68-3.65 (s, 2H), 2.75-2.67 (m, 1H), 2.58-2.52 (m, 4H), 2.47 (t, J=4.7, 4H), 1.63-1.57 (m, 4H), 1.45-1.39 (m, 2H), 1.04 (d, J=6.6, 6H).

Example 15

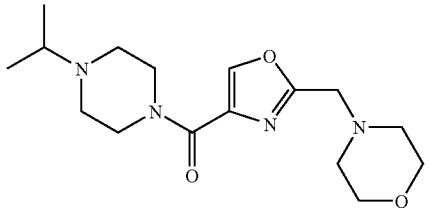

(4-Isopropyl-piperazin-1-yl)-(2-morpholin-4-ylmethyl-oxazol-4-yl)-methanone.

Step A. 2-Morpholin-4-ylmethyl-oxazole-4-carboxylic acid ethyl ester. The title compound was prepared in a manner similar to that described in Example 14, Step B. MS (ESI): exact mass calcd. for $C_{11}H_6N_2O_4$, 240.11; m/z found, 241.4 [M+H]$^+$.

Step B. 2-Morpholin-4-ylmethyl-oxazole-4-carboxylic acid. The title compound was prepared in a manner similar to that described in Example 14, Step C.

Step C. (4-Isopropyl-piperazin-1-yl)-(2-morpholin-4-yl-methyl-oxazol-4-yl)-methanone. The title compound was prepared in a manner similar to that described in Example 14, Step D. MS (ESI): exact mass calcd. for $C_{16}H_{26}N_4O_3$, 322.20; m/z found, 323.5 [M+H]$^+$. $^1$H NMR (500 MHz, CDCl$_3$): 8.13 (s, 1H), 4.10-4.00 (m, 2H), 3.76-3.71 (m, 6H), 3.70 (s, 2H), 2.75-2.68 (m, 1H), 2.60-2.52 (m, 8H), 1.05 (d, J=6.6, 6H).

Example 16

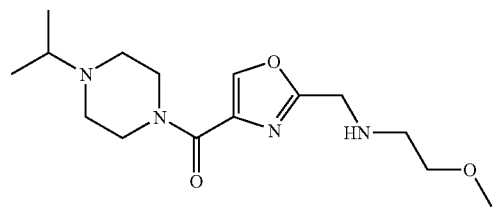

(4-Isopropyl-piperazin-1-yl)-{2-[(2-methoxy-ethylamino)-methyl]-oxazol-4-yl}-methanone.

Step A. 2-[(2-Methoxy-ethylamino)-methyl]-oxazole-4-carboxylic acid ethyl ester. The title compound was prepared in a manner similar to that described in Example 14, Step B.

Step B. 2-[(2-Methoxy-ethylamino)-methyl]-oxazole-4-carboxylic acid. The title compound was prepared in a manner similar to that described in Example 14, Step C. MS (ESI): exact mass calcd. for $C_8H_{12}N_2O_4$, 200.08; m/z found, 201.3 [M+H]$^+$.

Step C. 2-{[tert-Butoxycarbonyl-(2-methoxy-ethyl)-amino]-methyl}-oxazole-4-carboxylic acid. To a solution of 2-[(2-methoxy-ethylamino)-methyl]-oxazole-4-carboxylic acid, lithium salt (1.20 g, 5.82 mmol) in THF (30 mL) was added N,N-diisopropylethylamine (2.02 mL, 11.6 mmol), followed by a solution of di-tert-butyl dicarbonate (2.54 g, 11.6 mmol) in THF (15 mL). The reaction mixture was stirred overnight at rt. The mixture was diluted with DCM (60 mL) and extracted with H$_2$O (50 mL). The aqueous phase was concentrated to yield the crude product (1.104 g).

Step D. [4-(4-Isopropyl-piperazine-1-carbonyl)-oxazol-2-ylmethyl]-(2-methoxy-ethyl)-carbamic acid tert-butyl ester. A mixture of the crude material from Step C (1.10 g, 3.67 mmol), 1-isopropyl-piperazine dihydrochloride (0.810 g, 4.03 mmol), 1-hydroxybenzotriazole (0.595 g, 4.40 mmol), and N-methylmorpholine (2.42 mL, 22.0 mmol) in DMF (20 mL) was stirred for 1 h. 1-(3-Dimethylaminopropyl)-3-ethylcarbodiimide hydrochloride (0.845 g, 4.40 mmol) was added and the mixture was stirred overnight. The reaction mixture was diluted with H$_2$O (500 mL) and extracted with DCM (3×60 mL). The combined organic extracts were washed with H$_2$O (3×300 mL), dried over Na$_2$SO$_4$, filtered and concentrated to yield the crude title compound (1.30 g). MS (ESI): exact mass calcd. for $C_{20}H_{34}N_4O_5$, 410.25; m/z found, 411.5 [M+H]$^+$.

Step E. (4-Isopropyl-piperazin-1-yl)-{2-[(2-methoxy-ethylamino)-methyl]-oxazol-4-yl}-methanone. To a solution of the crude product from Step D in anhydrous dioxane (25 mL) was added 2 M HCl in dioxane (15 mL). The reaction mixture was stirred overnight and then was concentrated under vacuum to yield the crude product (0.240 g), which was purified on a silica gel column using 0-5% 2 M NH$_3$ in MeOH/DCM to give the title compound (0.050 g, 6%). MS (ESI): exact mass calcd. for $C_{15}H_{26}N_4O_3$, 310.20; m/z found, 311.5 [M+H]⁺. ¹H NMR (500 MHz, CDCl₃): 8.08 (s, 1H), 4.10-4.01 (m, 2H), 3.94 (s, 2H), 3.76-3.69 (m, 2H), 3.52-3.48 (m, 2H), 3.34 (s, 3H), 2.83-2.80 (m, 2H), 2.74-2.67 (m, 1H), 2.58-2.51 (m, 4H), 1.04 (d, J=6.6, 6H).

Example 17

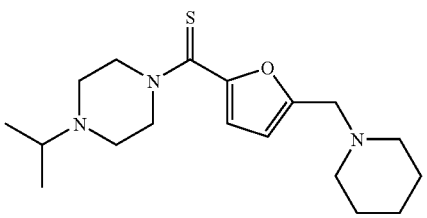

(4-Isopropyl-piperazin-1-yl)-(5-piperidin-1-ylmethyl-furan-2-yl)-methanethione.

A solution of (4-isopropyl-piperazin-1-yl)-(5-piperidin-1-ylmethyl-furan-2-yl)-methanone (Example 1, 1 equiv.) and Lawesson's reagent (2.1 equiv.) in THF is heated at reflux (70° C.) for 48 h. The reaction is cooled to room temperature and the solvent is removed in vacuo. Chromatography of the residue on a silica gel column using 1-6% 2 M NH₃ in MeOH/DCM) provides the title compound.

Example 18

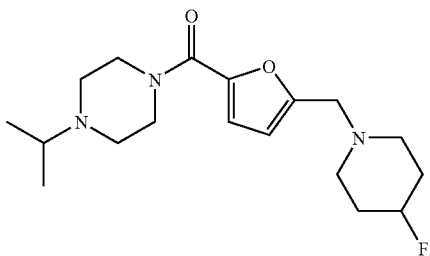

[5-(4-Fluoro-piperidin-1-ylmethyl)-furan-2-yl]-(4-isopropyl-piperazin-1-yl)-methanone.

The title compound was prepared in a manner similar to that described in Example 1, Step B. ¹H NMR (500 MHz, CDCl₃): 6.88 (d, J=3.4, 1H), 6.28 (d, J=3.4, 1H), 4.71-4.60 (m, 1H), 3.77 (br s, 4H), 3.59 (s, 2H), 2.74-2.69 (m, 1H), 2.63-2.58 (m, 2H), 2.55 (t, J=5.0, 4H), 2.47-2.42 (m, 2H), 1.94-1.84 (m, 4H), 1.04 (d, J=6.6, 6H).

Example 19

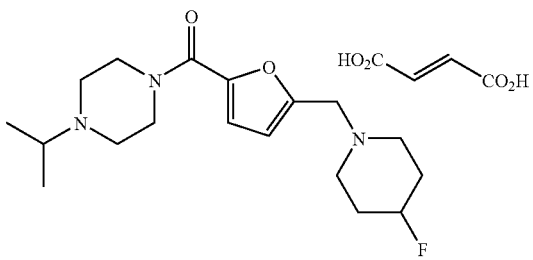

[5-(4-Fluoro-piperidin-1-ylmethyl)-furan-2-yl]-(4-isopropyl-piperazin-1-yl)-methanone, fumarate salt.

To a solution of the amine (0.495 g, 1.48 mmol) in EtOH (5 mL) was heated with a warmed solution of fumaric acid (0.171 g, 1.0 eq.) in EtOH (4 mL). The resulting homogeneous solution was concentrated in vacuo to provide 0.609 g (90%) of the fumarate salt. ¹H NMR (500 MHz, DMSO-d₆): 6.89 (d, J=3.3, 1H), 6.41 (d, J=3.3, 1H), 4.71-4.59 (m, 1H), 3.63 (br s, 4H), 3.54 (s, 2H), 3.41-3.35 (m, 2H), 2.74-2.71 (m, 1H), 2.49-2.44 (m, 4H), 2.34-2.30 (m, 2H), 1.86-1.65 (m, 4H), 0.97 (d, J=6.6, 6H).

BIOLOGY EXAMPLE

A. Transfection of Cells with Human Histamine Receptor

Cells were grown to about 70% to 80% confluence and removed from the plate with trypsin and pelleted in a clinical centrifuge. The pellet was then re-suspended in 400 μL of complete media and transferred to an electroporation cuvette with a 0.4 cm gap between the electrodes (Bio-Rad #165-2088). One μg supercoiled H₃ receptor cDNA was added to the cells and mixed gently. The voltage for the electroporation was set at 0.25 kV and the capacitance was set at 960 μF. After electroporation the cells were diluted with 10 mL of complete media and were plated onto four 10 cm dishes at the following ratios: 1:20, 1:10, 1:5, and 1:2. The cells were allowed to recover for 24 h before adding 600 μg G-418. Colonies that survived selection were grown and tested. SK-N-MC cells were used because they give efficient coupling for inhibition of adenylate cyclase. The clones that gave the most robust inhibition of adenylate cyclase in response to histamine were used for further study.

B. [³H]-N-Methylhistamine Binding

Cell pellets from histamine H₃ receptor-expressing SK-N-MC cells were homogenized in 50 mM Tris HCl/0.5 mM EDTA. Supernatants from an 800 g spin were collected and were recentrifuged at 30,000 g for 30 min. Pellets were re-homogenized in 50 mM Tris/5 mM EDTA (pH 7.4). Membranes were incubated with 0.8 nM [³H]-N-methylhistamine plus/minus test compounds for 60 min at 25° C. and were harvested by rapid filtration over GF/C glass fiber filters (pre-treated with 0.3% polyethylenimine) followed by four washes with buffer. Filters were added to 5 mL of scintillation cocktail, and the signal was then counted on a liquid scintillation counter. Non-specific binding was defined with 10 μM histamine. $pK_i$ values were calculated based on a $K_D$ of 0.8 nM and a liquid concentration ([L]) of 0.8 nM according to the formula $K_i=(IC_{50})/(1+([L]/(KD)))$. Data are presented in Table 1.

TABLE 1

Biological Data.

| EX | $K_i$ (nM) |
|---|---|
| 1 | 2 |
| 2 | 144 |
| 3 | 114 |
| 4 | 16 |
| 5 | 26 |
| 6 | 5 |
| 7 | 3 |
| 8 | 29 |
| 9 | 34 |
| 10 | 162 |
| 11 | 151 |
| 12 | 3000 |
| 13 | 2000 |
| 14 | 1000 |
| 15 | 3000 |
| 16 | 2000 |
| 19 | 64 |

What is claimed is:

1. A compound having histamine $H_3$ receptor modulating activity of formula (I):

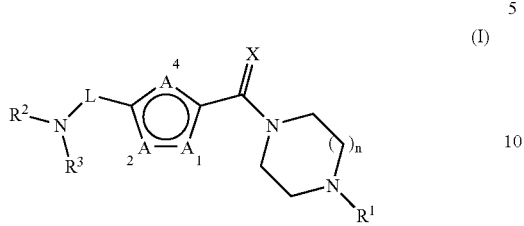

wherein $R^1$, optionally mono- or di-substituted with $R^s$, is selected from the group consisting of —H, —$C_{1-7}$alkyl, —$C_{2-7}$alkenyl, —$C_{2-7}$alkynyl, and —$C_{3-7}$cycloalkyl;

$R^s$ is independently selected from the group consisting of —$C_{1-6}$alkyl, —$C_{2-6}$alkenyl, —$C_{3-6}$cycloalkyl, phenyl, pyridyl, furanyl, thienyl, benzyl, pyrimidinyl, pyrrolyl, halo, —OH, —$OC_{1-6}$alkyl, —$OC_{3-6}$cycloalkyl, -Ophenyl, -Obenzyl, —SH, —$SC_{1-6}$alkyl, —$SC_{3-6}$cycloalkyl, -Sphenyl, -Sbenzyl, —CN, —$NO_2$, —N($R^m$)$R^n$ (wherein $R^m$ and $R^n$ are independently H or $C_{1-4}$alkyl), —(C=O)N($R^m$)$R^n$, —(C=O)$C_{1-4}$alkyl, —$SCF_3$, —$OCF_3$, —$CF_3$, —$COOC_{1-4}$alkyl, and —COOH;

n is 1 or 2;

X is O or S;

the A-containing ring is furan;

L is —$C_{1-4}$alkylene-;

$R^2$, optionally mono- or di-substituted with $R^q$, is independently selected from the group consisting of —H, —$C_{1-7}$alkyl, —$C_{2-7}$alkenyl, —$C_{2-7}$alkynyl, —$C_{3-7}$cycloalkyl, phenyl, benzyl, pyridinyl, pyrimidinyl, furanyl, thienyl, pyrrolyl, and a 5-, 6-, or 7-membered monocyclic non-aromatic heterocyclic ring having 1 or 2 heteroatom members selected from O, S, —N=, >NH, and >$NC_{1-4}$alkyl, having 0, 1, or 2 double bonds; and $R^3$, optionally mono- or di-substituted with $R^q$ is independently selected from the group consisting of —$C_{1-7}$alkyl, —$C_{2-7}$alkenyl, —$C_{2-7}$alkynyl, —$C_{3-7}$cycloalkyl, phenyl, benzyl, pyridinyl, pyrimidinyl, furanyl, thienyl, pyrrolyl, and a 5-, 6-, or 7-membered monocyclic non-aromatic heterocyclic ring having 1 or 2 heteroatom members selected from O, S, —N=, >NH, and >$NC_{1-4}$alkyl, having 0, 1, or 2 double bonds;

$R^q$ is independently selected from the group consisting of —$C_{1-6}$alkyl, —$C_{2-6}$alkenyl, —$C_{3-6}$cycloalkyl, phenyl, pyridyl, furanyl, thienyl, benzyl, pyrimidinyl, pyrrolyl, halo, —OH, —$OC_{1-6}$alkyl, —$OC_{3-6}$cycloalkyl, -Ophenyl, -Obenzyl, —SH, —$SC_{1-6}$alkyl, —$SC_{3-6}$cycloalkyl, -Sphenyl, -Sbenzyl, —CN, —$NO_2$, —N($R^y$)$R^z$ (wherein $R^y$ and $R^z$ are independently selected from H and $C_{1-4}$alkyl; or $R^y$ and $R^z$ may be taken together with the nitrogen of attachment to form a 5-, 6-, or 7-membered monocyclic heterocyclic ring having 1 or 2 additional heteroatom members selected from O, S, —N=, >NH, and >$NC_{1-4}$alkyl, said ring optionally substituted with halo or —$C_{1-4}$alkyl), —(C=O)N($R^y$)$R^z$, —(C=O)$C_{1-4}$alkyl, —$SCF_3$, —$OCF_3$, —$CF_3$, and —$COOC_{1-4}$alkyl, and —COOH;

or, alternatively $R^2$ and $R^3$ may be taken together with the nitrogen of attachment to form a ring, said ring selected from the group consisting of:

i) a 4-7 membered non-aromatic heterocyclic ring said heterocyclic ring having 0 or 1 additional heteroatom members separated from the nitrogen of attachment by at least one carbon member and selected from O, S, —N=, >NH, and >$NR^{pp}$, having 0, 1, or 2 double bonds, having 0, 1, or 2 carbon members which is a carbonyl, having 0, 1, or 2 substituents $R^p$; and ii) a benzo or pyrido fused 4-7 membered non-aromatic heterocyclic ring said heterocyclic ring having 0 or 1 additional heteroatom members separated from the nitrogen of attachment by at least one carbon member and selected from O, S, —N=, >NH, and >$NR^{pp}$, having 0 or 1 additional double bonds, having 0, 1, or 2 carbon members which is a carbonyl, and having 0, 1, or 2 substituents $R^p$;

$R^p$ is independently selected from the group consisting of —$C_{1-6}$alkyl, —$C_{2-6}$alkenyl, —$C_{3-6}$cycloalkyl, phenyl, pyridyl, furanyl, thienyl, benzyl, pyrimidinyl, pyrrolyl, halo, —OH, —$OC_{1-6}$alkyl, —$OC_{3-6}$cycloalkyl, -Ophenyl, -Obenzyl, —SH, —$SC_{1-6}$alkyl, —$SC_{3-6}$cycloalkyl, -Sphenyl, -Sbenzyl, —CN, —$NO_2$, —N($R^y$)$R^z$ (wherein $R^y$ and $R^z$ are independently selected from H and $C_{1-4}$alkyl; or $R^y$ and $R^z$ may be taken together with the nitrogen of attachment to form a 5-, 6-, or 7-membered monocyclic heterocyclic ring having 1 or 2 additional heteroatom members selected from O, S, —N=, >NH, and >$NC_{1-4}$alkyl, said ring optionally substituted with halo or —$C_{1-4}$alkyl), —(C=O)N($R^y$)$R^z$, —(C=O)$C_{1-4}$alkyl, —$SCF_3$, —$OCF_3$, —$CF_3$, —$COOC_{1-4}$alkyl, and —COOH;

$R^{pp}$ is independently selected from the group consisting of —$C_{1-6}$alkyl, —$C_{2-6}$alkenyl, —$C_{3-6}$cycloalkyl, phenyl, pyridyl, benzyl, pyrimidinyl, pyrrolyl, —(C=O)N($R^y$)$R^z$, —(C=O)$C_{1-4}$alkyl, —$COOC_{1-4}$alkyl, and —$COOC_{1-4}$benzyl;

and enantiomers, diastereomers, and pharmaceutically acceptable salts and amides thereof.

2. The compound of claim 1 wherein $R^1$ is selected from the group consisting of —H, methyl, ethyl, propyl, isopropyl, butyl, isobutyl, propenyl, propargyl, cyclopropyl, cyclobutyl, cyclopentyl, hydroxyethyl, methoxyethyl, and diethylaminoethyl.

3. The compound of claim 1 wherein $R^1$ is selected from the group consisting of methyl, ethyl, isopropyl, and cyclopropyl.

4. The compound of claim 1 wherein $R^1$ is isopropyl.

5. The compound of claim 1 wherein n is 1.

6. The compound of claim 1 wherein X is O.

7. The compound of claim 1 wherein L is methylene.

8. The compound of claim 1 wherein $R^2$ is independently selected from the group consisting of —H, methyl, ethyl, propyl, isopropyl, butyl, isobutyl, methoxyethyl, hydroxyethyl, piperidinylethyl, morpholinylethyl, pyridylethyl, diethylaminoethyl, propenyl, propargyl, cyclopropyl, cyclopentyl, cyclohexyl, phenyl, benzyl, pyridinyl, pyrrolyl, pyrrolidinyl, piperidinyl, morpholinyl, thiomorpholinyl, and azepanyl.

9. The compound of claim 1 wherein $R^2$ is independently selected from the group consisting of —H, methyl, ethyl, propyl, isopropyl, butyl, isobutyl, methoxyethyl, cyclopropyl, piperidinylethyl, morpholinylethyl, pyridylethyl, and diethylaminoethyl.

10. The compound of claim 1 wherein $R^2$ is independently selected from the group consisting of —H, methyl, and methoxyethyl.

11. The compound of claim 1 wherein $R^3$ is independently selected from the group consisting of methyl, ethyl, propyl, isopropyl, butyl, isobutyl, methoxyethyl, hydroxyethyl, piperidinylethyl, morpholinylethyl, pyridylethyl, diethylaminoethyl, propenyl, propargyl, cyclopropyl, cyclopentyl, cyclohexyl, phenyl, benzyl, pyridinyl, pyrrolyl, pyrrolidinyl, piperidinyl, morpholinyl, thiomorpholinyl, and azepanyl.

12. The compound of claim 1 wherein $R^3$ is independently selected from the group consisting of methyl, ethyl, propyl, isopropyl, butyl, isobutyl, methoxyethyl, cyclopropyl, piperidinylethyl, morpholinylethyl, pyridylethyl, and diethylaminoethyl.

13. The compound of claim 1 wherein $R^3$ is independently selected from the group consisting of methyl and methoxyethyl.

14. The compound of claim 1 wherein $R^2$ and $R^3$ may be taken together with the nitrogen of attachment to form a ring selected from the group consisting of piperidine, morpholine, thiomorpholine, piperazine, and pyrrolidine.

15. The compound of claim 1 wherein $R^2$ and $R^3$ may be taken together with the nitrogen of attachment to form a ring selected from the group consisting of piperidine, morpholine, and piperazine.

16. The compound of claim 1 wherein $R^2$ and $R^3$ may be taken together with the nitrogen of attachment to form 4-fluoropiperidine.

17. The compound of claim 1 wherein $R^2$ and $R^3$ may be taken together with the nitrogen of attachment to form a ring selected from the group consisting of piperidine and morpholine.

18. The compound of claim 1 wherein $R^{pp}$ is —$C_{1-6}$alkyl.

19. A compound selected from the group consisting of:
(4-Isopropyl-piperazin-1-yl)-(5-piperidin-1-ylmethyl-furan-2-yl)-methanone;
(4-Isopropyl-piperazin-1-yl)-(5-morpholin-4-ylmethyl-furan-2-yl)-methanone;
(4-Isopropyl-piperazin-1-yl)-{5-[(2-methoxy-ethylamino)-methyl]-furan-2-yl}-methanone;
(4-Isopropyl-piperazin-1-yl)-(5-piperidin-1-ylmethyl-furan-2-yl)-methanethione;
[5-(4-Fluoro-piperidin-1-ylmethyl)-furan-2-yl]-(4-isopropyl-piperazin-1-yl)-methanone; and
[5-(4-Fluoro-piperidin-1-ylmethyl)-furan-2-yl]-(4-isopropyl-piperazin-1-yl)-methanone, fumarate salt.

20. A compound selected which is:
(4-Isopropyl-piperazin-1-yl)-(5-piperidin-1-ylmethyl-furan-2-yl)-methanone.

21. The compound of claim 1 wherein said pharmaceutically acceptable salt is an effective amino addition salt.

22. The compound of claim 1 wherein said pharmaceutically acceptable salt is selected from the group consisting of hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate.

23. A pharmaceutical composition comprising a pharmaceutically acceptable carrier and a therapeutically effective amount of compound having histamine $H_3$ receptor modulator activity of formula (I):

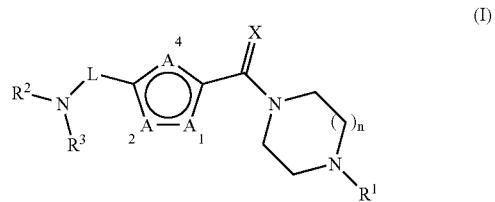

wherein
$R^1$, optionally mono- or di-substituted with $R^s$, is selected from the group consisting of —H, —$C_{1-7}$alkyl, —$C_{2-7}$alkenyl, —$C_{2-7}$alkynyl, and —$C_{3-7}$cycloalkyl;
$R^s$ is independently selected from the group consisting of —$C_{1-6}$alkyl, —$C_{2-6}$alkenyl, —$C_{3-6}$cycloalkyl, phenyl, pyridyl, furanyl, thienyl, benzyl, pyrimidinyl, pyrrolyl, halo, —OH, —$OC_{1-6}$alkyl, —$OC_{3-6}$cycloalkyl, -Ophenyl, -Obenzyl, —SH, —$SC_{1-6}$alkyl, —$SC_{3-6}$cycloalkyl, -Sphenyl, -Sbenzyl, —CN, —$NO_2$, —$N(R^m)R^n$ (wherein $R^m$ and $R^n$ are independently H or $C_{1-4}$alkyl), —(C=O)$N(R^m)R^n$, —(C=O)$C_{1-4}$alkyl, —$SCF_3$, —$OCF_3$, —$CF_3$, —$COOC_{1-4}$alkyl, and —COOH;
n is 1 or 2;
X is O or S;
the A-containing ring is furan;
L is —$C_{1-4}$alkylene-;
$R^2$, optionally mono- or di-substituted with $R^q$, is independently selected from the group consisting of —H, —$C_{1-7}$alkyl, —$C_{2-7}$alkenyl, —$C_{2-7}$alkynyl, —$C_{3-7}$cycloalkyl, phenyl, benzyl, pyridinyl, pyrimidinyl, furanyl, thienyl, pyrrolyl, and a 5-, 6-, or 7-membered monocyclic non-aromatic heterocyclic ring having 1 or 2 heteroatom members selected from O, S, —N=, >NH, and >$NC_{1-4}$alkyl, having 0, 1, or 2 double bonds; and
$R^3$, optionally mono- or di-substituted with $R^q$, is independently selected from the group consisting of —$C_{1-7}$alkyl, —$C_{2-7}$alkenyl, —$C_{2-7}$alkynyl, —$C_{3-7}$cycloalkyl, phenyl, benzyl, pyridinyl, pyrimidinyl, furanyl, thienyl, pyrrolyl, and a 5-, 6-, or 7-membered monocyclic non-aromatic heterocyclic ring having 1 or 2 heteroatom members selected from O, S, —N=, >NH, and >$NC_{1-4}$alkyl, having 0, 1, or 2 double bonds;
$R^q$ is independently selected from the group consisting of —$C_{1-6}$alkyl, —$C_{2-6}$alkenyl, —$C_{3-6}$cycloalkyl, phenyl, pyridyl, furanyl, thienyl, benzyl, pyrimidinyl, pyrrolyl, halo, —OH, —$OC_{1-6}$alkyl, —$OC_{3-6}$cycloalkyl, -Ophenyl, -Obenzyl, —SH, —$SC_{1-6}$alkyl, —$SC_{3-6}$cycloalkyl, -Sphenyl, -Sbenzyl, —CN, —$NO_2$, —$N(R^y)R^z$ (wherein $R^y$ and $R^z$ are independently selected from H and $C_{1-4}$alkyl; or $R^y$ and $R^z$ may be taken together with the nitrogen of attachment to form a 5-, 6-, or 7-membered monocyclic heterocyclic ring having 1 or 2 additional heteroatom members selected from O, S, —N=, >NH, and >$NC_{1-4}$alkyl, said ring optionally substituted with halo or —$C_{1-4}$alkyl), —(C=O)$N(R^y)R^z$, —(C=O)$C_{1-4}$alkyl, —$SCF_3$, —$OCF_3$, —$CF_3$, and —$COOC_{1-4}$alkyl, and —COOH;
or, alternatively
$R^2$ and $R^3$ may be taken together with the nitrogen of attachment to form a ring, said ring selected from the group consisting of:
i) a 4-7 membered non-aromatic heterocyclic ring said heterocyclic ring having 0 or 1 additional heteroatom members separated from the nitrogen of attachment by at least one carbon member and selected from O, S, —N═, >NH, and >NR$^{pp}$, having 0, 1, or 2 double bonds, having 0, 1, or 2 carbon members which is a carbonyl, having 0, 1, or 2 substituents R$^p$; and ii) a benzo or pyrido fused 4-7 membered non-aromatic heterocyclic ring said heterocyclic ring having 0 or 1 additional heteroatom members separated from the nitrogen of attachment by at least one carbon member and selected from O, S, —N═, >NH, and >NR$^{pp}$, having 0 or 1 additional double bonds, having 0, 1, or 2 carbon members which is a carbonyl, and having 0, 1, or 2 substituents R$^p$;

R$^p$ is independently selected from the group consisting of —C$_{1-6}$alkyl, —C$_{2-6}$alkenyl, —C$_{3-6}$cycloalkyl, phenyl, pyridyl, furanyl, thienyl, benzyl, pyrimidinyl, pyrrolyl, halo, —OH, —OC$_{1-6}$alkyl, —OC$_{3-6}$cycloalkyl, -Ophenyl, -Obenzyl, —SH, —SC$_{1-6}$alkyl, —SC$_{3-6}$cycloalkyl, -Sphenyl, -Sbenzyl, —CN, —NO$_2$, —N(R$^y$)R$^z$ (wherein R$^y$ and R$^z$ are independently selected from H and C$_{1-4}$alkyl; or R$^y$ and R$^z$ may be taken together with the nitrogen of attachment to form a 5-, 6-, or 7-membered monocyclic heterocyclic ring having 1 or 2 additional heteroatom members selected from O, S, —N═, >NH, and >NC$_{1-4}$ alkyl, said ring optionally substituted with halo or —C$_{1-4}$alkyl), —(C═O)N(R$^y$)R$^z$, —(C═O)C$_{1-4}$ alkyl, —SCF$_3$, —OCF$_3$, —CF$_3$, —COOC$_{1-4}$alkyl, and —COOH;

R$^{pp}$ is independently selected from the group consisting of —C$_{1-6}$alkyl, —C$_{2-6}$alkenyl, —C$_{3-6}$cycloalkyl, phenyl, pyridyl, benzyl, pyrimidinyl, pyrrolyl, —(C═O)N(R$^y$)R$^z$, —(C═O)C$_{1-4}$alkyl, —COOC$_{1-4}$ alkyl, and —COOC$_{1-4}$benzyl;

and enantiomers, diastereomers, and pharmaceutically acceptable salts and amides thereof.

\* \* \* \* \*